(12) United States Patent
Chou et al.

(10) Patent No.: US 10,147,188 B2
(45) Date of Patent: Dec. 4, 2018

(54) METHOD AND SYSTEM FOR SURGICAL TOOL LOCALIZATION DURING ANATOMICAL SURGERY

(71) Applicant: SONY CORPORATION, Tokyo (JP)

(72) Inventors: Chen-Rui Chou, San Jose, CA (US); Ming-Chang Liu, San Jose, CA (US)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/856,298

(22) Filed: Dec. 28, 2017

(65) Prior Publication Data

US 2018/0122070 A1    May 3, 2018

Related U.S. Application Data

(63) Continuation of application No. 14/860,914, filed on Sep. 22, 2015.
(Continued)

(51) Int. Cl.
*G06K 9/00* (2006.01)
*G06T 7/00* (2017.01)
(Continued)

(52) U.S. Cl.
CPC ............ *G06T 7/0012* (2013.01); *A61B 34/20* (2016.02); *A61B 90/37* (2016.02); *G06T 5/20* (2013.01);
(Continued)

(58) Field of Classification Search
CPC ........... G06T 7/0012; G06T 7/74; G06T 5/20; A61B 90/37
See application file for complete search history.

(56) References Cited

U.S. PATENT DOCUMENTS

| 5,792,147 A | 8/1998 | Evans et al. |
| 8,447,096 B2 | 5/2013 | Klein et al. |

(Continued)

FOREIGN PATENT DOCUMENTS

| WO | 2009/045827 A2 | 4/2009 |
| WO | 2014/093824 A1 | 6/2014 |

OTHER PUBLICATIONS

Notice of Allowance for U.S. Appl. No. 14/860,914, dated Oct. 18, 2017, 08 pages.
(Continued)

*Primary Examiner* — Gregory M Desire
(74) *Attorney, Agent, or Firm* — Chip Law Group

(57) ABSTRACT

Various aspects of a method and system to localize surgical tools during anatomical surgery are disclosed herein. In accordance with an embodiment of the disclosure, the method is implementable in an image-processing engine, which is communicatively coupled to an image-capturing device that captures one or more video frames. The method includes determination of one or more physical characteristics of one or more surgical tools present in the one or more video frames, based on one or more color and geometric constraints. Thereafter, two-dimensional (2D) masks of the one or more surgical tools are detected, based on the one or more physical characteristics of the one or more surgical tools. Further, poses of the one or more surgical tools are estimated, when the 2D masks of the one or more surgical tools are occluded at tips and/or ends of the one or more surgical tools.

17 Claims, 10 Drawing Sheets

Related U.S. Application Data

(60) Provisional application No. 62/118,043, filed on Feb. 19, 2015.

(51) Int. Cl.
*A61B 90/00* (2016.01)
*G06T 5/20* (2006.01)
*G06T 7/73* (2017.01)
*A61B 34/20* (2016.01)
*G06T 7/11* (2017.01)

(52) U.S. Cl.
CPC ............... *G06T 7/11* (2017.01); *G06T 7/73* (2017.01); *G06T 7/74* (2017.01); *A61B 2034/2065* (2016.02); *A61B 2090/374* (2016.02); *A61B 2090/3762* (2016.02); *G06K 2209/057* (2013.01); *G06T 2207/10016* (2013.01); *G06T 2207/10024* (2013.01); *G06T 2207/20004* (2013.01); *G06T 2207/30004* (2013.01); *G06T 2207/30021* (2013.01)

(56) References Cited

U.S. PATENT DOCUMENTS

| | | | |
|---|---|---|---|
| 9,259,844 B2 * | 2/2016 | Xu | B25J 15/0608 |
| 9,601,025 B2 | 3/2017 | Kesavadas et al. | |
| 9,633,428 B2 * | 4/2017 | Simanovsky | G06T 7/0004 |
| 2003/0208122 A1 * | 11/2003 | Melkent | A61B 5/06 |
| | | | 600/426 |
| 2004/0002642 A1 | 1/2004 | Dekel et al. | |
| 2009/0088634 A1 | 4/2009 | Zhao et al. | |
| 2009/0220131 A1 | 9/2009 | Cinquin et al. | |
| 2009/0259123 A1 | 10/2009 | Navab et al. | |
| 2012/0184846 A1 | 7/2012 | Izatt et al. | |
| 2013/0211232 A1 * | 8/2013 | Murphy | A61B 1/0005 |
| | | | 600/411 |
| 2014/0046341 A1 | 2/2014 | Dicarlo | |
| 2014/0171787 A1 | 6/2014 | Garbey et al. | |
| 2014/0341424 A1 | 11/2014 | Reiter et al. | |
| 2014/0371527 A1 | 12/2014 | Sato | |
| 2015/0297313 A1 | 10/2015 | Reiter et al. | |
| 2016/0022125 A1 * | 1/2016 | Nicolau | A61B 5/062 |
| | | | 600/424 |

OTHER PUBLICATIONS

Non-Final Office Action for U.S. Appl. No. 14/860,914, dated May 19, 2017, 16 pages.
Chun-Ju Chen et al., "Image Tracking of Laparoscopic Instrument Using Spiking Neural Networks", 2013 13th International Conference on Control, Automation and Systems (ICCAS 2013), Gwangju, Korea, Oct. 20-23, 2013 pp. 951-955.
Max Allan et al., "Detection and Localization of Instruments in Minimally Invasive Surgery", Division of Surgery and Interventional Science, UCL Medical School, 04 pages.
International Search Report and Written Opinion Received for PCT Application No. PCT/US2016/018035, dated Apr. 22, 2016, 12 pages.

* cited by examiner

METHOD AND SYSTEM FOR SURGICAL TOOL LOCALIZATION DURING ANATOMICAL SURGERY

CROSS-REFERENCE TO RELATED APPLICATIONS/INCORPORATION BY REFERENCE

The present application is a continuation application of U.S. patent application Ser. No. 14/860,914, filed Sep. 22, 2015, which claims priority from U.S. Provisional Patent Application Ser. No. 62/118,043 filed Feb. 19, 2015, the entire contents of which are hereby incorporated by reference.

FIELD

Various embodiments of the disclosure relate to a method and system for surgical tool localization. More specifically, various embodiments of the disclosure relate to a method and system for surgical tool localization during anatomical surgery.

BACKGROUND

With recent advancements in the medical sciences, various surgical and diagnostic procedures can now be performed by use of minimally invasive techniques. Such minimally invasive techniques may require small incisions to insert endoscopic or laparoscopic surgical instruments through the patient's skin into the body cavity. The endoscopic or laparoscopic surgical instruments may include an inbuilt camera to capture video footage of the body cavity. The video footage may be displayed to a physician in real time to enable the physician to perform the surgical or diagnostic procedure on a designated anatomical region within the body cavity.

In certain scenarios, a clear view of one or more portions of a surgical instrument within the body cavity may be occluded by one or more portions of another surgical instrument, surgical gauze, tissue, and/or smoke/mist within the body cavity. This may cause a hindrance to the physician when the physician performs the surgical or diagnostic procedure. Hence, there is a need for real-time analysis of video footage of surgical or diagnostic procedures to monitor and localize surgical instruments within the body cavity.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

A method and a system to localize surgical tools during anatomical surgery substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Figure 1:
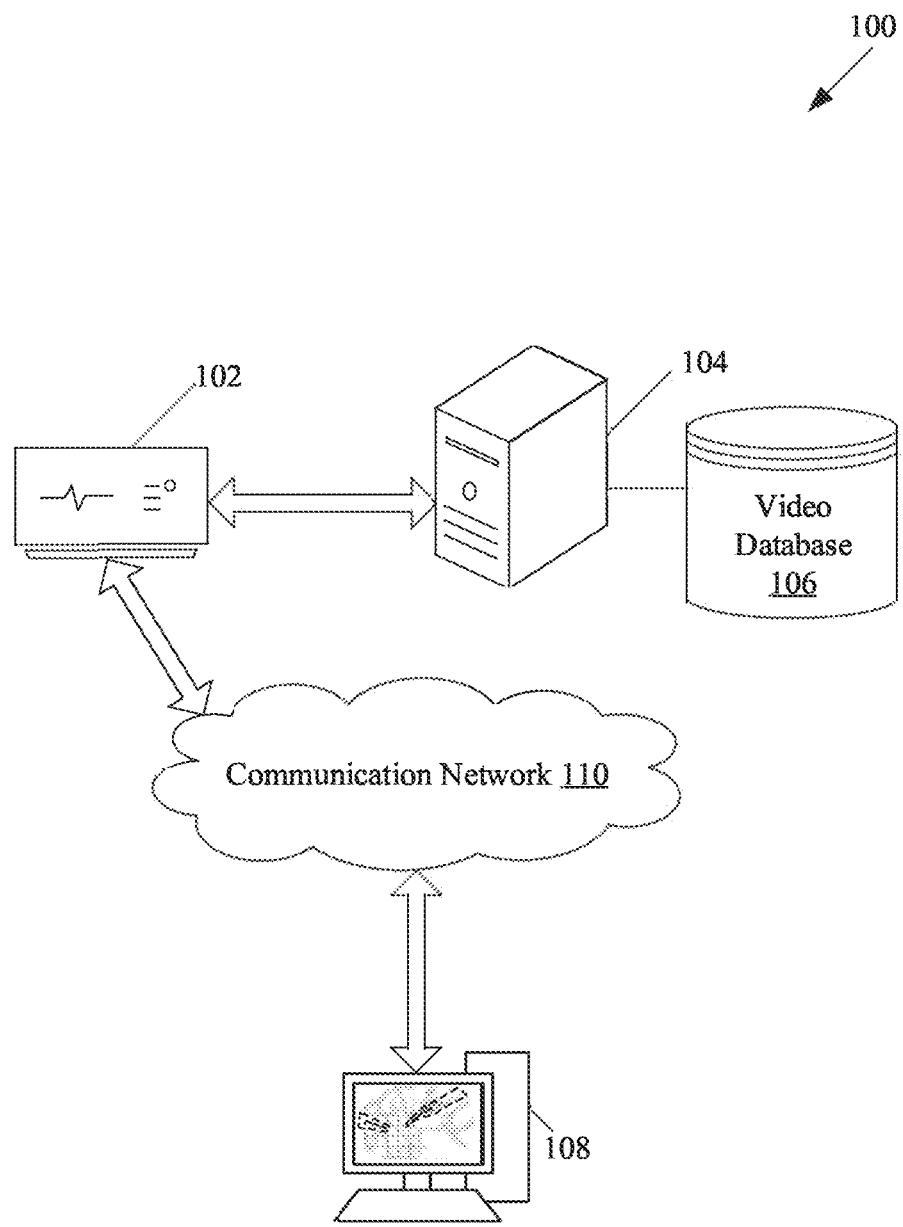
FIG. 1 is a block diagram that illustrates a network environment, in accordance with an embodiment of the disclosure.

The following described implementations may be found in the disclosed method and system for surgical tool localization during anatomical surgery. Exemplary aspects of the disclosure may include a method implementable in an image-processing engine. The image-processing engine may be communicatively coupled to an image-capturing device. The image-capturing device may be configured to capture one or more video frames. The method may include the determination of one or more physical characteristics of one or more surgical tools present in the one or more video frames. The determination of the one or more physical characteristics may be based on one or more color and geometric constraints. Thereafter, two-dimensional (2D) masks of the one or more surgical tools present in the one or more video frames may be detected, based on the determined one or more physical characteristics of the one or more surgical tools. Further, poses of the one or more surgical tools in the one or more video frames may be estimated, when the 2D masks of the one or more surgical tools are occluded at tips and/or ends of the one or more surgical tools.

In accordance with an embodiment, one or more smoke blocks may be removed from the one or more video frames to generate a smoke-free video frame, when the one or more video frames is occluded with the one or more smoke blocks. In accordance with an embodiment, one or more smoke regions may be detected in each of a set of video frames prior to the one or more video frames. The removal of the one or more smoke blocks from the one or more video frames may be based on an accumulated intensity of a set of pixels in the detected one or more smoke regions in each of the set of video frames prior to the one or more video frames.

In accordance with an embodiment, contour evolution may be performed based on color characteristics of the one or more surgical tools in the detected 2D masks of the one or more surgical tools in the smoke-free video frame. The performance of the contour evolution may be further based on a curvature and an intensity variance of regions inside and/or outside a contour of the detected 2D masks in the smoke-free video frame. Further, segmentation of the smoke-free video frame may be performed to detect the one or more surgical tools in the smoke-free video frame, based on the contour evolution.

In accordance with an embodiment, adaptive color filtering may be performed on each region of the one or more video frames. The adaptive color filtering may correspond to one or more color constraints, and may be based on intensity of pixels in each region of the one or more video frames. The adaptive color filtering may be performed based on one or more of an opp2-color intensity-based filtering and/or a normalized opp2-color intensity-based filtering. In accordance with an embodiment, the detection of the 2D masks of the one or more surgical tools present in the one or more video frames may be based on the adaptive color filtering.

In accordance with an embodiment, locations of the tips and/or the ends of the one or more surgical tools in the one or more video frames may be estimated, based on an analysis of the detected 2D masks of the one or more surgical tools. The analysis of the detected 2D masks may be performed along a first directional vector that may extend along a longitudinal principal axis of the detected 2D masks of the one or more surgical tools. In accordance with an embodiment, a centroid of the locations of the tips and/or the ends of the one or more surgical tools in the one or more video frames may be determined. The locations of the tips and/or the ends of the one or more surgical tools in the one or more video frames may be re-estimated, when the centroid lies outside the detected 2D masks of the one or more surgical tools or the centroid is occluded. The re-estimation of the locations of the tips and/or the ends of the one or more surgical tools may be based on an analysis of the detected 2D masks of the one or more surgical tools, along a second directional vector. The second directional vector may be at a predetermined angle with respect to the first directional vector.

In accordance with an embodiment, the estimation of the poses of the one or more surgical tools may be based on the estimated locations of the ends of the one or more surgical tools, when the tips of the one or more surgical tools are occluded. Further, the estimation of the poses of the one or more surgical tools may be based on the estimated locations of the tips of the one or more surgical tools, when the centroid and/or the ends of the one or more surgical tools is/are occluded.

In accordance with an embodiment, one or more image-capture settings of the image-capturing device may be adjusted based on the estimation of the poses of the one or more surgical tools in the one or more video frames. Examples of the one or more image-capture settings may include, but are not limited to, an auto-exposure, an auto-focus, an auto-white-balance, or an auto-illumination.

In accordance with an embodiment, the current one or more video frames may be displayed to a user (such as a physician) in real-time, via a user interface (UI) during the anatomical surgery. The one or more surgical tools may be masked or highlighted in the current one or more video frames displayed to the user, via the UI. In accordance with an embodiment, a notification indicative of an occlusion of the one or more surgical tools, at the tips and/or ends of the one or more surgical tools, may be generated. Examples of the notification may include, but are not limited to, an audio alert, a textual alert, a visual alert, or a haptic alert.

FIG. 1 is a block diagram that illustrates a network environment, in accordance with an embodiment of the disclosure. With reference to FIG. 1, there is shown a network environment 100. The network environment 100 may include a surgical device 102, an image-processing server 104, a video database 106, a user terminal 108, and a communication network 110. The surgical device 102 may be communicatively coupled to the image-processing server 104, the video database 106, and the user terminal 108, via the communication network 110.

The surgical device 102 may comprise suitable logic, circuitry, interfaces, and/or code that may be configured to perform one or more surgical procedures and/or diagnostic analyses associated with one or more anatomical regions of a patient. Examples of the surgical device 102 may include, but are not limited to, a minimally invasive surgical/diagnostic device, a minimal incision surgical/diagnostic device, and/or an endoscopic/laparoscopic surgical/diagnostic device.

In accordance with an embodiment, the surgical device 102 may further include an image-capturing device (not shown in FIG. 1). The image-capturing device may capture one or more video frames of an anatomical region of a patient when a surgery or diagnostic procedure is performed on the anatomical region. Alternatively, the surgical device 102 may be communicatively coupled to the image-capturing device, via the communication network 110. Examples of the image-capturing device may include, but are not limited to, an endoscopic/laparoscopic camera, a medical resonance imaging (MRI) device, a computer tomography (CT) scanning device, a minimally invasive medical imaging device, and/or a minimal incision medical imaging device.

The image-processing server 104 may comprise one or more servers that may provide image-processing services to one or more subscribed electronic devices, such as the user terminal 108 and/or the surgical device 102. In accordance with an embodiment, the image-processing server 104 may be configured to analyze the one or more video frames captured by the image-capturing device while the surgical or diagnostic procedure is performed. The image-processing server 104 may then perform detection of surgical tools in the one or more video frames, based on the analysis of the one or more video frames. In accordance with an embodiment, the image-processing server 104 may be implemented as a plurality of cloud-based resources by use of several technologies that are well known to those skilled in the art. Further, the image-processing server 104 may be associated with a single or multiple service providers. Examples of the one or more servers may include, but are not limited to, Apache™ HTTP Server, Microsoft® Internet Information Services (IIS), IBM® Application Server, Sun Java™ System Web Server, and/or a file server.

A person with ordinary skill in the art will understand that the scope of the disclosure is not limited to implementation of the image-processing server 104 and the surgical device 102 as separate entities. In accordance with an embodiment, the functionalities of the image-processing server 104 may be implemented by the surgical device 102, without departure from the scope of the disclosure.

The video database 106 may store a repository of the one or more video frames captured by the image-capturing device. In accordance with an embodiment, the video database 106 may be communicatively coupled to the image-processing server 104. The video database 106 may receive the one or more video frames, via the image-processing server 104, when the image-capturing device captures the one or more video frames. In accordance with an embodiment, the video database 106 may be implemented by use of various database technologies known in the art. Examples of the video database 106 may include, but are not limited to, Microsoft® SQL Server, Oracle®, IBM DB2®, Microsoft Access®, PostgreSQL®, MySQL®, and/or SQLite®. In accordance with an embodiment, the image-processing server 104 may connect to the video database 106, based on one or more protocols. Examples of such one or more protocols may include, but are not limited to, Open Database Connectivity (ODBC)® protocol and Java Database Connectivity (JDBC)® protocol.

A person with ordinary skill in the art will understand that the scope of the disclosure is not limited to implementation of the image-processing server 104 and the video database 106 as separate entities. In accordance with an embodiment, the functionalities of the video database 106 may be implemented by the image-processing server 104, without departure from the scope of the disclosure.

The user terminal 108 may comprise suitable logic, circuitry, interfaces, and/or code that may be configured to present a user interface (UI) to display the one or more video frames to a user, such as a physician. In accordance with an embodiment, the user terminal 108 may display the one or more video frames, in real-time, while the surgical or diagnostic procedure is performed on the anatomical region of the patient. The user terminal 108 may be further configured to display the one or more surgical tools that are localized in each of the one or more video frames by the image-processing server 104. Examples of the user terminal 108 may include, but are not limited to, a smartphone, a camera, a tablet computer, a laptop, a wearable electronic device, a television, an Internet Protocol Television (IPTV), and/or a Personal Digital Assistant (PDA) device.

A person with ordinary skill in the art will understand that the scope of the disclosure is not limited to implementation of the user terminal 108 and the image-processing server 104 as separate entities. In accordance with an embodiment, the functionalities of the image-processing server 104 may be implemented by the user terminal 108 without departure from the scope of the disclosure. For example, the image-processing server 104 may be implemented as an application program that runs and/or is installed on the user terminal 108.

A person with ordinary skill in the art will further understand that in accordance with an embodiment, the user terminal 108 may be integrated with the surgical device 102. Alternatively, the user terminal 108 may be communicatively coupled to the surgical device 102 and a user, such as a physician, of the user terminal 108 may control the surgical device 102, via the UI of the user terminal 108.

The communication network 110 may include a medium through which the surgical device 102 and/or the user terminal 108 may communicate with one or more servers, such as the image-processing server 104. Examples of the communication network 110 may include, but are not limited to, the Internet, a cloud network, a Wireless Fidelity (Wi-Fi) network, a Wireless Local Area Network (WLAN), a Local Area Network (LAN), a plain old telephone service (POTS), and/or a Metropolitan Area Network (MAN). Various devices in the network environment 100 may be configured to connect to the communication network 110, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

In operation, the image-capturing device may be configured to capture one or more video frames. The image-processing server 104 may be configured to determine one or more physical characteristics of one or more surgical tools present in a particular video frame of the captured one or more video frames. In accordance with an embodiment, the determination of the one or more physical characteristics of the one or more surgical tools may be based on one or more color and geometric constraints. Thereafter, the image-processing server 104 may detect two-dimensional (2D) masks of the one or more surgical tools present in the video frame, based on the determined one or more physical characteristics of the one or more surgical tools. The image-processing server 104 may be further configured to estimate poses of the one or more surgical tools in the video frame, when the 2D masks of the one or more surgical tools are occluded at tips and/or ends of the one or more surgical tools.

In accordance with an embodiment, the image-processing server 104 may be configured to analyze a set of video frames prior to the video frame. The image-processing server 104 may detect one or more smoke regions in each video frame from the set of video frames prior to the video frame. Further, the image-processing server 104 may determine an accumulated intensity of a set of pixels in the detected one or more smoke regions in each of the set of video frames prior to the video frame. Thereafter, the image-processing server 104 may remove one or more smoke blocks from the video frame to generate a smoke-free video frame, when the video frame is occluded with the one or more smoke blocks. In accordance with an embodiment, the removal of the one or more smoke blocks may be based on the accumulated intensity of the set of pixels in the detected one or more smoke regions in each of the set of video frames prior to the video frame.

In accordance with an embodiment, contour evolution may be performed based on color characteristics of the one or more surgical tools in the detected 2D masks of the one or more surgical tools in the smoke-free video frame. Performance of the contour evolution may be further based on a curvature and an intensity variance of regions inside and/or outside a contour of the detected 2D masks in the smoke-free video frame. Further, segmentation of the smoke-free video frame may be performed to detect the one or more surgical tools in the smoke-free video frame, based on the contour evolution.

In accordance with an embodiment, adaptive color filtering may be performed on each region in the video frame. The adaptive color filtering may correspond to the one or more color constraints, and may be based on intensity of pixels in each region in the video frame. The adaptive color filtering may be performed based on an opp2-color intensity-based filtering and/or a normalized opp2-color intensity-based filtering. In accordance with an embodiment, the detection of the 2D masks of the one or more surgical tools present in the video frame may be based on the adaptive color filtering.

In accordance with an embodiment, locations of the tips and/or the ends of the one or more surgical tools in the video frame may be estimated. The estimation may be based on an analysis of the detected 2D masks of the one or more surgical tools. The analysis of the detected 2D masks may be performed along a first directional vector (hereinafter interchangeably referred to as "first principal direction" or "first principal axis") that may extend along a longitudinal principal axis of the detected 2D masks of the one or more surgical tools. In accordance with an embodiment, a centroid of the locations of the tips and/or the ends of the one or more surgical tools in the video frame may be determined. The locations of the tips and/or the ends of the one or more surgical tools in the video frame may be re-estimated when the centroid lies outside the detected 2D masks of the one or more surgical tools and/or the centroid is occluded. The re-estimation of the locations of the tips and/or the ends of the one or more surgical tools may be based on an analysis of the detected 2D masks of the one or more surgical tools, along a second directional vector (hereinafter interchangeably referred to as "second principal direction" or "second principal axis") of the detected 2D masks. The second principal direction may be at a predetermined angle with respect to the first principal direction. For example, the second principal direction may be orthogonal with respect to the first principal direction.

In accordance with an embodiment, the estimation of the poses of the one or more surgical tools may be based on the estimated locations of the ends of the one or more surgical tools, when the tips of the one or more surgical tools are occluded. Further, the estimation of the poses of the one or more surgical tools may be based on the estimated locations of the tips of the one or more surgical tools, when the centroid and/or the ends of the one or more surgical tools is/are occluded.

In accordance with an embodiment, the image-processing server 104 may be configured to adjust one or more image-capture settings of the image-capturing device in real time, based on the determination of the smoke region. Examples of the one or more image-capture settings may include, but are not limited to, an auto-exposure, an auto-focus, an auto-white-balance, and/or an auto-illumination.

In accordance with an embodiment, the image-processing server 104 may be further configured to display the one or more video frames to a user (such as a physician), via the UI of the user terminal 108, while the surgical or diagnostic procedure is performed. The frames may include the current video frame. The one or more surgical tools localized in the current video frame may be masked or highlighted within the current video frame displayed to the user, via the UI. In accordance with an embodiment, the image-processing server 104 may be further configured to generate a notification indicative of the localization of the one or more surgical tools in the current video frame. The notification may also indicate an extent and/or type of occlusion of each surgical tool in the current video frame. The image-processing server 104 may transmit the notification to the surgical device 102, and/or the user terminal 108. The notification may be presented to the user (such as the physician) by the surgical device 102 and/or the user terminal 108. Examples of the notification may include, but are not limited to, an audio alert, a textual alert, a visual alert, and/or a haptic alert.

Figure 2:
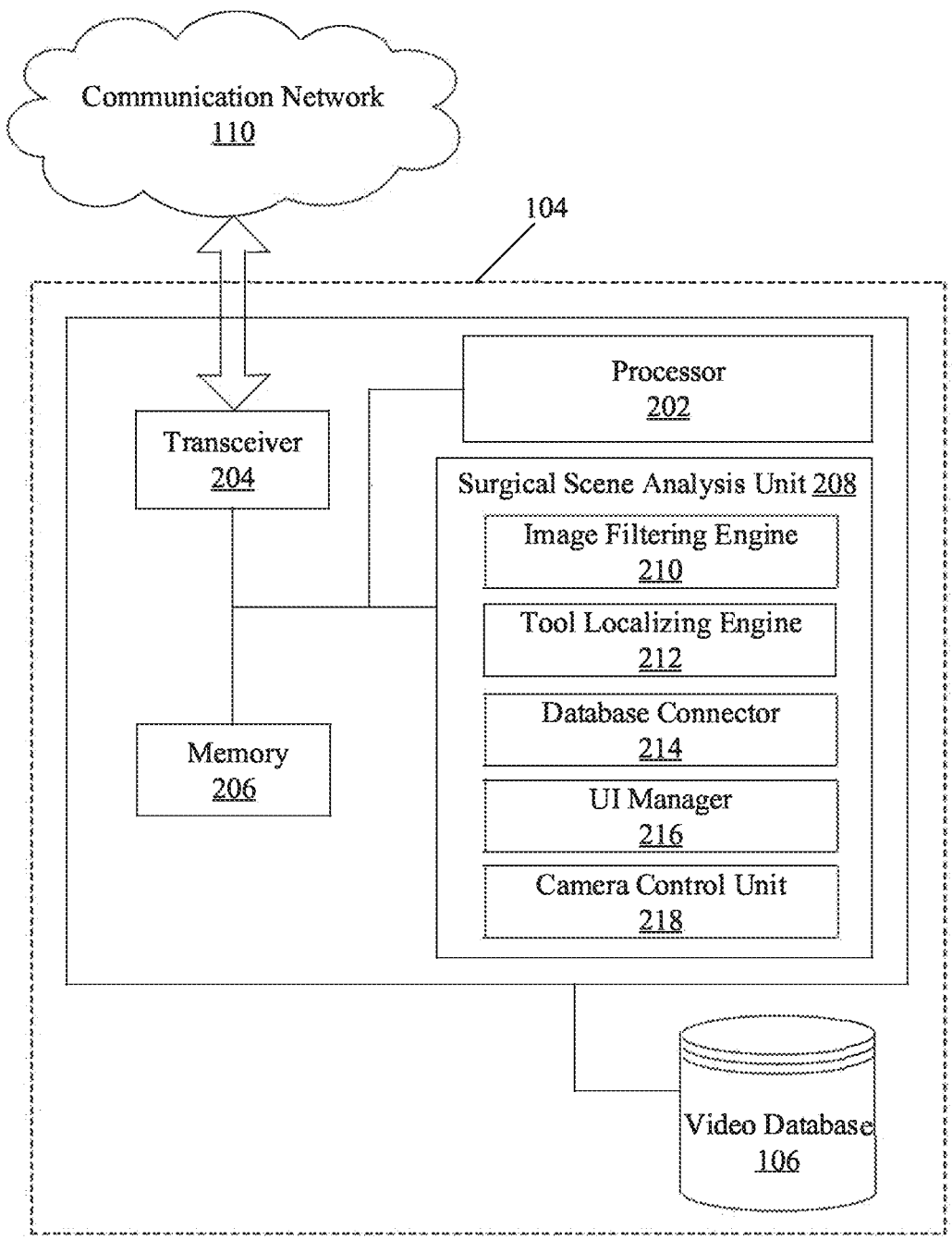
FIG. 2 is a block diagram that illustrates an exemplary image-processing server, in accordance with an embodiment of the disclosure.

FIG. 2 is a block diagram that illustrates an exemplary image-processing server, in accordance with an embodiment of the disclosure. FIG. 2 is explained in conjunction with elements from FIG. 1. With reference to FIG. 2, there is shown the image-processing server 104. The image-processing server 104 may comprise one or more processors, such as a processor 202, one or more transceivers, such as a transceiver 204, a memory 206, and a surgical scene analysis unit 208. The surgical scene analysis unit 208 may include an image-filtering engine 210, a tool localizing engine 212, a database connector 214, a UI manager 216, and a camera control unit 218. In accordance with an embodiment, the image-processing server 104 may be communicatively coupled to the video database 106, through the communication network 110, via the transceiver 204. Alternatively, the image-processing server 104 may include the video database 106. For example, the video database 106 may be implemented within the memory 206.

The processor 202 may be communicatively coupled to the transceiver 204, the memory 206, and the surgical scene analysis unit 208. The transceiver 204 may be configured to communicate with the surgical device 102 and the user terminal 108, via the communication network 110.

The processor 202 may comprise suitable logic, circuitry, interfaces, and/or code that may be configured to execute a set of instructions stored in the memory 206. The processor 202 may be implemented, based on a number of processor technologies known in the art. Examples of the processor 202 may be an X86-based processor, a Reduced Instruction Set Computing (RISC) processor, an Application-Specific Integrated Circuit (ASIC) processor, a Complex Instruction Set Computing (CISC) processor, and/or other processors.

The transceiver 204 may comprise suitable logic, circuitry, interfaces, and/or code that may be configured to communicate with the user terminal 108 and/or the surgical device 102, via the communication network 110 (as shown in FIG. 1). The transceiver 204 may implement known technologies to support wired or wireless communication of the image-processing server 104 with the communication network 110. Various components of the transceiver 204 may include, but are not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The transceiver 204 may communicate with networks, such as the Internet, an Intranet and/or a wireless network, such as a cellular telephone network, a wireless local area network (LAN) and/or a metropolitan area network (MAN), via wireless communication. The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (such as IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The memory 206 may comprise suitable logic, circuitry, and/or interfaces that may be configured to store a machine code and/or a computer program with at least one code section executable by the processor 202. In accordance with an embodiment, the memory 206 may be further configured to store the one or more video frames captured by the image-capturing device. Examples of implementation of the memory 206 may include, but are not limited to, Random Access Memory (RAM), Read Only Memory (ROM), Hard Disk Drive (HDD), and/or a Secure Digital (SD) card.

The surgical scene analysis unit 208 may comprise suitable logic, circuitry, interfaces, and/or code that may be configured to analyze and process the one or more video frames captured by the image-capturing device. In accordance with an embodiment, the surgical scene analysis unit 208 may be a part of the processor 202. Alternatively, the surgical scene analysis unit 208 may be implemented as a separate processor or circuitry in the image-processing server 104. In accordance with an embodiment, the surgical scene analysis unit 208 and the processor 202 may be implemented as an integrated processor or a cluster of processors that perform the functions of the surgical scene analysis unit 208 and the processor 202. In accordance with another embodiment, the surgical scene analysis unit 208 may be implemented as a computer program code, stored in the memory 206, which on execution by the processor 202 may perform the functions of the surgical scene analysis unit 208.

The image-filtering engine 210 may comprise suitable logic, circuitry, interfaces, and/or code that may be configured to analyze the one or more video frames to detect two-dimensional (2D) masks of one or more surgical tools present in each video frame. In accordance with an embodiment, the image-filtering engine 210 may be configured to determine one or more physical characteristics of the one or more surgical tools present in a particular video frame of the one or more video frames. The determination of the one or more physical characteristics of the one or more tools may be based on one or more color and geometric constraints. The image-filtering engine 210 may detect the 2D masks of the one or more surgical tools in the video frame, based on the determined one or more physical characteristics of the one or more surgical tools. In accordance with an embodiment, the image-filtering engine 210 may be further configured to remove one or more smoke blocks from the video frame to generate a smoke-free video frame, when the video frame is occluded with the one or more smoke blocks.

The tool localizing engine 212 may comprise suitable logic, circuitry, interfaces, and/or code that may be configured to estimate poses of the one or more surgical tools in the video frame. In accordance with an embodiment, the tool localizing engine 212 may be configured to analyze the detected 2D masks of the one or more surgical tools in the video frame. This detection may estimate the poses of the one or more surgical tools in the video frame. The tool localizing engine 212 may be further configured to estimate locations of tips and/or ends of the one or more surgical tools in the video frame. The tool localizing engine 212 may then determine a centroid of the locations of the tips and/or ends of the one or more surgical tools. Further, the tool localizing engine 212 may re-estimate the locations of the tips and/or ends of the one or more surgical tools, when the centroid lies outside the detected 2D masks of the one or more surgical tools, and/or the centroid is occluded. In accordance with an embodiment, the poses of the one or more surgical tools may be estimated, based on the estimated locations of the ends, when the tips are occluded. Further, the poses of the one or more surgical tools may be estimated, based on the estimated locations of the tips, when the centroid and/or the ends is/are occluded.

A person with ordinary skill in the art will understand that the scope of the disclosure should not be limited to the implementation of the image-filtering engine 210 and the tool localizing engine 212 as separate entities. In accordance with an embodiment, the image-filtering engine 210 and the tool localizing engine 212 may be integrated into a single entity that may be configured to perform the functionalities of both image-filtering engine 210 and the tool localizing engine 212.

The database connector 214 may comprise suitable logic, circuitry, interfaces, and/or code that may be configured to provide the surgical scene analysis unit 208 with access and connectivity to the video database 106. In accordance with an embodiment, the database connector 214 may establish a database session between the surgical scene analysis unit 208 and the video database 106. Examples of one or more communication protocols used to establish the database session may include, but are not limited to, Open Database Connectivity (ODBC)® protocol and Java Database Connectivity (JDBC)® protocol.

The UI manager 216 may comprise suitable logic, circuitry, interfaces, and/or code that may be configured to manage the UI presented on the user terminal 108. In accordance with an embodiment, the UI manager 216 may provide a surgical scene interface to a user (such as a physician) of the user terminal 108. The surgical scene interface may be presented to the user on a display device of the user terminal 108, via the UI of the user terminal 108. In accordance with an embodiment, the surgical scene interface may be configured to display the one or more video frames including the current video frame to the user. The one or more surgical tools localized in the current video frame may be masked or highlighted within the current video frame displayed to the user, via the surgical scene interface.

The camera control unit 218 may comprise suitable logic, circuitry, interfaces, and/or code that may be configured to communicate with the image-capturing device to adjust one or more image-capture settings of the image-capturing device. In accordance with an embodiment, the camera control unit 218 may be configured to determine such values of the one or more image-capture settings, which may be suitable or optimal to capture the one or more video frames, based on the localization of the one or more surgical tools. Thereafter, the camera control unit 218 may be configured to transmit the determined values of the one or more image-capture settings to the image-capturing device, via the transceiver 204. The image-capturing device may adjust its image-capturing settings, based on the corresponding values that are sent by the camera control unit 218. Examples of the one or more image-capture settings may include, but are not limited to, an auto-exposure, an auto-focus, an auto-white-balance, and/or an auto-illumination.

In operation, a physician may perform a surgical or diagnostic procedure on an anatomical region of a patient, by use of the surgical device 102 and one or more surgical instruments. Examples of the one or more surgical instruments may include, but are not limited to, endoscopic catheters, surgical forceps, surgical incision instruments, and/or surgical gauze. Examples of the surgical or diagnostic procedures may include, but are not limited to, minimally invasive surgery/diagnosis, minimal incision surgery/diagnosis, laparoscopy, and/or endoscopy. In accordance with an embodiment, the surgical or diagnostic procedure may be automated and performed by a surgical robot, without supervision or direction from the physician. In accordance with an embodiment, the surgical or diagnostic procedure may be semi-automated and performed by the surgical robot, with one or more input signals and/or commands from the physician. In accordance with an embodiment, the image-capturing device (not shown in FIG. 1) may be communicatively coupled to (or included within) the surgical device 102. The image-capturing device may capture one or more video frames of the anatomical region in real time, while the surgical or diagnostic procedure is performed on the anatomical region. Thereafter, the surgical device 102 (or the image-capturing device) may transmit the captured video frames to the image-processing server 104, via the communication network 110.

The transceiver 204, in the image-processing server 104, may be configured to receive the one or more video frames from the surgical device 102, via the communication network 110. In accordance with an embodiment, the one or more video frames may be received as real-time streamed media content by use of a communication protocol, such as a real-time transport protocol and/or a real-time streaming protocol (RTSP). The database connector 214 may be configured to establish a database session with the video database 106 and store the received video frames in the video database 106. Further, the video frames may also be stored in the memory 206.

The image-filtering engine 210 may be configured to analyze the one or more video frames. In accordance with an embodiment, the video frames may be analyzed in a batch mode (offline processing), when a predetermined number of video frames are received from the surgical device 102. In accordance with an embodiment, the video frames may be analyzed on a real-time basis (online processing), upon receipt of each new video frame. The image-filtering engine 210 may retrieve the video frames from the memory 206 or the video database 106 for analysis of the video frames.

In accordance with an embodiment, before analysis of a current video frame to detect 2D masks of the one or more surgical tools, the image-filtering engine 210 may be configured to determine whether the current video frame is occluded with one or more smoke blocks. The image-filtering engine 210 may be configured to remove the one or more smoke blocks from the current video frame to generate a smoke-free video frame, when the video frame is occluded with the one or more smoke blocks. In accordance with an embodiment, the image-filtering engine 210 may detect one or more smoke regions in each video frame from a set of video frames prior to the current video frame. Thereafter, the image-filtering engine 210 may determine an accumulated intensity of a set of pixels in the detected one or more smoke regions in each video frame from the set of video frames prior to the current video frame. The removal of the one or more smoke blocks from the current video frame may be based on the determined accumulated intensity of the set of pixels. For instance, the image-filtering engine 210 may subtract the accumulated intensity of the set of pixels, which correspond to the detected one or more smoke regions, from the intensity of the corresponding pixels in the current video frame. This may be done to generate the smoke-free video frame. A person with ordinary skill in the art will understand that the removal of the one or more smoke blocks from the current video frame may be skipped when the accumulated intensity of the set of pixels is within a predetermined intensity threshold range. An exemplary flow diagram that illustrates a method to remove the one or more smoke blocks from the current video frame to generate the smoke-free video frame is explained in FIG. 5.

In accordance with an embodiment, the image-filtering engine 210 may be configured to analyze the current video frame (or the smoke-free video frame) to determine one or more physical characteristics of the one or more surgical tools present in the current video frame. The determination of the one or more physical characteristics of the one or more surgical tools may be based on one or more color and geometric constraints. Thereafter, the image-filtering engine 210 may detect the 2D masks of the one or more surgical tools in the video frame, based on the one or more physical characteristics of the one or more surgical tools.

In accordance with an embodiment, the image-filtering engine 210 may apply the one or more color constraints by performing an adaptive color filtering, based on intensity of pixels in each region in the current video frame (or the smoke-free video frame). The adaptive color filtering may be performed based on an opp2-color intensity-based filtering or a normalized opp2-color intensity-based filtering, on each region in the current video frame (or the smoke-free video frame). In accordance with an embodiment, the image-filtering engine 210 may analyze the following conditions to perform the adaptive color filtering:

$$\text{Condition 1: } I_{gray} \geq 100 \text{ and } \frac{opp2}{\mu_{opp2}} < 0.6$$

$$\text{Condition 2: } I_{gray} < 100 \text{ and } \frac{opp2_{norm}}{\mu_{opp2_{norm}}} < 0.5$$

where, "$I_{gray}$" represents grey scale intensity of a pixel of the video frame;

"opp2" represents opp2 color component of the pixel, given by:

$$opp2 = |R - G| \quad (1)$$

"$opp2_{norm}$" represents normalized opp2 color component of the pixel, given by:

$$opp2_{norm} = \frac{|R - G|}{R + G + B} \quad (2)$$

"R", "G", and "B" represent the red, green, and blue color components of the pixel.

In accordance with an embodiment, the image-filtering engine 210 may analyze the conditions, "Condition 1" and "Condition 2", to determine one or more regions of interest that may correspond to the one or more surgical tools within the video frame. The image-filtering engine 210 may analyze the condition, "Condition 1", for regions with brighter pixels in the video frame (such as regions that include pixels with gray-scale intensity greater than or equal to 100). Further, the image-filtering engine 210 may check the condition, "Condition 2", for regions with darker pixels in the video frame (such as regions that include pixels with gray-scale intensity less than 100). As is evident, the condition, "Condition 1", may entail the performance of an opp2-color intensity-based filtering in brighter regions of the video frame. Further, the condition, "Condition 2", may entail the performance of a normalized opp2-color intensity-based filtering in darker regions of the video frame. A person with ordinary skill in the art will understand that regions, which include the one or more surgical tools, may encompass pixels with marginal differences in their red and green color components. Hence, opp2-color intensity-based filtering may be used to determine the one or more regions of interest, which may correspond to the one or more surgical tools in the video frame. However, opp2-color intensity-based filtering may not be efficient to detect the one or more surgical tools in darker regions of the video frame. The one or more surgical tools may be effectively detected in darker regions by use of normalized opp2-color intensity-based filtering. Therefore, the regions of interest that may correspond to the one or more surgical tools in the video frame may be determined by use of the adaptive color filtering, based on both of the opp2-color intensity-based filtering and the normalized opp2-color intensity-based filtering.

In accordance with an embodiment, the image-filtering engine 210 may be configured to apply the one or more geometric constraints on the determined one or more regions of interest to detect the 2D masks of the one or more surgical tools in the video frame. For instance, the image-filtering engine 210 may check whether the size of each region of interest is greater than a predetermined size threshold. Further, the image-filtering engine 210 may perform edge detection on the determined one or more regions of interest.

Thereafter, the image-filtering engine 210 may check whether the number of edges within each region of interest is greater than a predetermined edge count. Further, the image-filtering engine 210 may determine whether the region of interest is located in an outside-in orientation in the video frame. The image-filtering engine 210 may designate the region of interest as a part of the 2D mask of the one or more surgical tools, if the region of interest satisfies the aforementioned size, edge, and/or orientation conditions. Thus, the detection of the 2D masks of the one or more surgical tools in the video frame may be based on the adaptive color filtering and/or the application of one or more geometric constraints on each region of the video frame.

In accordance with an embodiment, the image-filtering engine 210 may be further configured to refine the detected 2D masks of the one or more surgical tools. This may be done to detect the one or more surgical tools in the current video frame. In accordance with an embodiment, the image-filtering engine 210 may be configured to determine contours in the detected 2D masks of the one or more surgical tools. Thereafter, the image-filtering engine 210 may perform contour evolution on the contours determined in the detected 2D masks of the one or more surgical tools in the current video frame (or the smoke-free video frame). The contour evolution may be performed based on color characteristics of the one or more surgical tools in the detected 2D masks of the one or more surgical tools. In accordance with an embodiment, the image-filtering engine 210 may use a level-set based technique to perform the contour evolution by use of equations (3) and (4), as follows:

$$\frac{\partial \phi}{\partial t} = |\nabla \phi| \cdot \left(\frac{\nabla \phi}{|\nabla \phi|}\right) - (u_0 - c_1)^2 + (u_0 - c_2)^2 \quad (3)$$

$$\frac{\partial \phi}{\partial t} = 0 \text{ at edges} \quad (4)$$

where, $$"\frac{\partial \phi}{\partial t}"$$

represents instantaneous slope of a tangent at a pixel on a contour;

$$"|\nabla \phi| \cdot \left(\frac{\nabla \phi}{|\nabla \phi|}\right)"$$

represents the mean curvature motion;
"$u_0$" represents intensity of the pixel;
"$c_1$" represents average intensity of pixels inside the contour; and
"$c_2$" represents average intensity of pixels outside the contour.

Thus, the image-filtering engine 210 may apply the differential equations (3) and (4) to perform the contour evolution on the detected 2D masks of the one or more surgical tools to refine the detected 2D masks. In accordance with an embodiment, the contour evolution may be based on a curvature and an intensity variance of regions inside and/or outside a contour of the detected 2D masks in the current video frame (or the smoke-free video frame). As is evident, the expression, $$"|\nabla \phi| \cdot \left(\frac{\nabla \phi}{|\nabla \phi|}\right)",$$

in the equation (3) may be used to penalize high curvature of a contour in a region of interest that corresponds to the detected 2D mask. Further, the expressions, "$(u_0-c_1)^2$" and "$(u_0-c_2)^2$", may be used to minimize the intensity variance inside and outside the contours in that region of interest, respectively. The equation (4) may be used to evolve the contour at edges in that region of interest. A person with ordinary skill in the art will understand that the color characteristics of the pixels in the region of interest may be used in accordance with the adaptive color filtering, as described above. For instance, in consideration of the performance of the contour evolution, the opp2 color intensity may be considered for brighter pixels (such as pixels with intensity greater than or equal to 100), while the normalized opp2 color intensity may be considered for darker pixels in the region of interest. Alternatively, the image-filtering engine 210 may determine an average pixel intensity of pixels in the region of interest. The image-filtering engine 210 may consider the opp2 color intensity of the pixels in the region of interest, when the average pixel intensity is high (such as greater than or equal to 100). Otherwise, the normalized opp2 color intensity of the pixels in the region of interest may be considered. An exemplary flow diagram that illustrates a method to refine the preliminary 2D masks of the one or more surgical tools in the current video frame is explained in FIG. 6.

In accordance with an embodiment, the image-filtering engine 210 may perform segmentation of the current video frame (or the smoke-free video frame), based on the performance of the contour evolution on the detected 2D masks of the one or more surgical tools. The image-filtering engine 210 may then detect the one or more surgical tools, based on the result of the segmentation process. Thus, the image-filtering engine 210 may refine the 2D masks of the one or more surgical tools to detect the one or more surgical tools in the current video frame.

In accordance with an embodiment, the tool localizing engine 212 may be configured to estimate poses of the one or more surgical tools in the video frame, when the 2D masks of the one or more surgical tools are occluded at the tips and/or ends of the one or more surgical tools. The tool localizing engine 212 may estimate the locations of the tips and/or ends of the one or more surgical tools in the video frame to estimate the poses of the one or more surgical tools. In accordance with an embodiment, the estimation of the location of the tips and/or ends may be based on an analysis of the detected 2D masks of the one or more surgical tools, along a first principal direction. In accordance with an embodiment, the first principal direction may extend along a longitudinal principal axis of the detected 2D masks of the one or more surgical tools. Further, the tool localizing engine 212 may determine a centroid of the locations of the tips and/or ends of the one or more surgical tools. In accordance with an embodiment, the tool localizing engine 212 may be further configured to re-estimate the locations of the tips and/or ends of the one or more surgical tools when the centroid lies outside the detected 2D masks of the one or more surgical tools, or the centroid is occluded. The re-estimation of the locations of the tips and/or ends may be based on an analysis of the 2D masks of the one or more surgical tools, along a second principal direction. The second principal direction may be at a predetermined angle with respect to the first principal direction. In accordance with an embodiment, the second principal direction may extend along a latitudinal principal axis, orthogonal to the first principal direction. In such a scenario, the predetermined angle may be a right angle (or "90 degrees"). However, a person with ordinary skill in the art will understand that the scope of the disclosure should not be limited to the predetermined angle as a right angle. The predetermined angle may be any other angle, such as an acute angle (or "0 to 90 degrees"), an obtuse angle (or "90 to 180 degrees"), or a reflex angle (or "180 to 360 degrees").

In accordance with an embodiment, the estimation of the poses of the one or more surgical tools may be based on the estimated (or re-estimated) location of the ends of the one or more surgical tools, when the tips of the one or more surgical tools are occluded. Further, the estimation of the poses of the one or more surgical tools may be based on the estimated (or re-estimated) locations of the tips of the one or more surgical tools, when the centroid and/or the ends of the one or more surgical tools is/are occluded. Exemplary scenarios of poses of one or more surgical tools in a video frame are explained in conjunction with FIGS. 7A to 7D. Further, an exemplary flow diagram that illustrates a method to estimate poses of one or more surgical tools in a video frame is explained in conjunction with FIG. 4.

A person with ordinary skill in the art will understand that the values of the various predetermined thresholds are exemplary values. The values of the predetermined thresholds may vary, based on implementation, software, hardware and/or user requirements, without deviation from the scope of the disclosure.

In accordance with an embodiment, the UI manager 216 may be configured to present a surgical scene interface to a user, such as a physician, of the user terminal 108. The surgical scene interface may be presented to the user on a display device of the user terminal 108, via the UI of the user terminal 108. In accordance with an embodiment, the surgical scene interface may be configured to display to the user the one or more video frames that include the current video frame. The one or more surgical tools localized in the current video frame may be masked or highlighted in the current video frame displayed to the user, via the surgical scene interface. An exemplary scenario of the surgical scene interface has been explained in FIG. 8.

In accordance with an embodiment, the UI manager 216 may be further configured to generate a notification that may signal the localization of the one or more surgical tools in the current video frame. The notification may also indicate an extent and/or type of occlusion of each surgical tool in the current video frame. The UI manager 216 may communicate the generated notification to the user terminal 108. The notification may be presented to the user, via the UI of the user terminal 108. In case of real-time or online analysis of the one or more video frames for localization of the one or more surgical tools, the UI manager 216 may also transmit the generated notification to the surgical device 102, via the transceiver 204. Examples of the notification may include, but are not limited to, an audio alert, a textual alert, a visual alert, and/or a haptic feedback.

In accordance with an embodiment, the camera control unit 218 may be configured to determine optimal values for one or more image-capture settings of the image-capturing device, based on the localization of the one or more surgical tools in the current video frame. Examples of the one or more image-capture settings may include, but are not limited to, an auto-exposure, an auto-focus, an auto-white-balance, or an auto-illumination. In accordance with an embodiment, the optimal values of the one or more image-capture settings may be determined, based on one or more conditions, such as a size of a region that encompasses the one or more surgical tools, an average intensity of pixels in that region, an extent of occlusion of the one or more surgical tools, or one or more features of that region. In an embodiment, the determination of the optimal values may also be based on user-specified criteria. The camera control unit 218 may be configured to transmit the optimal values of the one or more image-capture settings to the image-capturing device, via the transceiver 204. The one or more image-capture settings of the image-capturing device may be adjusted, based on the respective optimal values sent by the camera control unit 218.

In accordance with an embodiment, the UI manager 216 may present the optimal values of the one or more image-capture settings to the user, via the UI of the user terminal 108. The UI manager 216 may be enable the user to confirm or adjust the optimal values, via the UI of the user terminal 108. The UI manager 216 may receive a user input indicative of a confirmation or an adjustment of the optimal values from the user terminal 108, via the transceiver 204. Thereafter, the camera control unit 218 may update the optimal values, based on the user input, and transmit the updated optimal values to the image-capturing device, via the transceiver 204. The one or more image-capture settings of the image-capturing device may be adjusted based on the updated optimal values received from the camera control unit 218.

Figure 3:
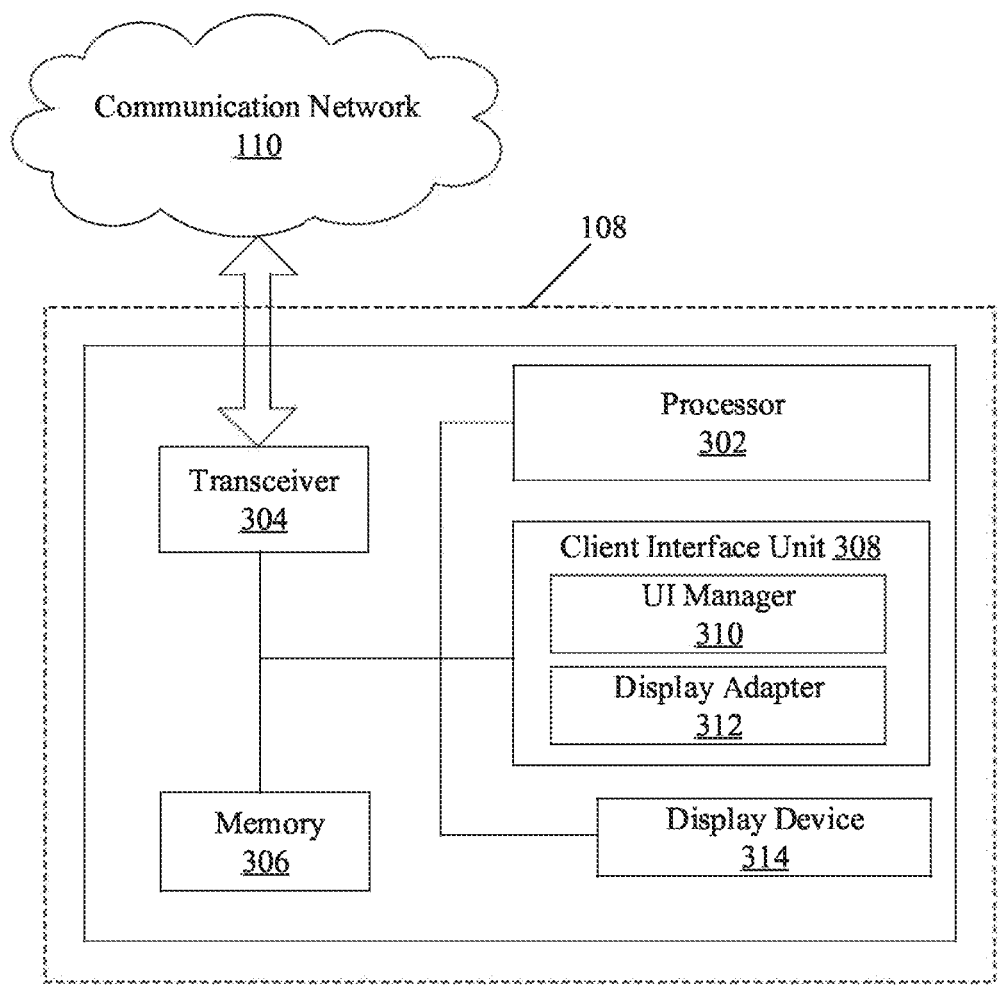
FIG. 3 is a block diagram that illustrates an exemplary user terminal, in accordance with an embodiment of the disclosure.

FIG. 3 is a block diagram that illustrates an exemplary user terminal, in accordance with an embodiment of the disclosure. FIG. 3 is explained in conjunction with elements from FIG. 1. With reference to FIG. 3, there is shown the user terminal 108. The user terminal 108 may comprise one or more processors, such as a processor 302, one or more transceivers, such as a transceiver 304, a memory 306, a client interface unit 308, and a display device 314. The client interface unit 308 may include a UI manager 310 and a display adapter 312. The processor 302 may be communicatively coupled to the transceiver 304, the memory 306, the client interface unit 308, and the display device 314. The transceiver 304 may be configured to communicate with the image-processing server 104 and/or the surgical device 102, via the communication network 110.

The processor 302 may comprise suitable logic, circuitry, interfaces, and/or code that may be configured to execute a set of instructions stored in the memory 306. The processor 302 may be implemented, based on a number of processor technologies known in the art. Examples of the processor 302 may be an X86-based processor, a Reduced Instruction Set Computing (RISC) processor, an Application-Specific Integrated Circuit (ASIC) processor, a Complex Instruction Set Computing (CISC) processor, and/or other processors.

The transceiver 304 may comprise suitable logic, circuitry, interfaces, and/or code that may be configured to communicate with the image-processing server 104 and/or the surgical device 102, via the communication network 110 (as shown in FIG. 1). The transceiver 304 may implement known technologies to support wired or wireless communication of the user terminal 108 with the communication network 110. The transceiver 304 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The transceiver 304 may communicate with networks, such as the Internet, an Intranet and/or a wireless network, such as a cellular telephone network, a wireless local area network (LAN) and/or a metropolitan area network (MAN), via wireless communication. The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (such as IEEE 802.11a, IEEE 802.11b, IEEE 802.11g and/or IEEE 802.11n), voice over Internet Protocol (VoIP), Wi-MAX, a protocol for email, instant messaging, and/or Short Message Service (SMS).

The memory 306 may comprise suitable logic, circuitry, and/or interfaces that may be configured to store a machine code and/or a computer program with at least one code section executable by the processor 302. Examples of implementation of the memory 306 may include, but are not limited to, Random Access Memory (RAM), Read Only Memory (ROM), Hard Disk Drive (HDD), and/or a Secure Digital (SD) card.

The client interface unit 308 may comprise suitable logic, circuitry, interfaces, and/or code that may be configured to render and manage one or more UIs presented on the user terminal 108. In accordance with an embodiment, the client interface unit 308 may be a part of the processor 302. Alternatively, the client interface unit 308 may be implemented as a separate processor or circuitry in the user terminal 108. For example, the client interface unit 308 may be implemented as a dedicated graphics processor or chipset, communicatively coupled to the processor 302. In accordance with an embodiment, the client interface unit 308 and the processor 302 may be implemented as an integrated processor, or a cluster of processors, which perform the functions of the client interface unit 308 and the processor 302. In accordance with an embodiment, the client interface unit 308 may be implemented as a computer program code, stored in the memory 306, which on execution by the processor 302 may perform the functions of the client interface unit 308.

The UI manager 310 may comprise suitable logic, circuitry, interfaces, and/or code that may be configured to manage the UI of the user terminal 108. In accordance with an embodiment, the UI manager 310 may be further configured to receive and process user input received, via the UI of the user terminal 108, via an input device (not shown) of the user terminal 108. In accordance with an embodiment, the input device may be communicatively coupled to (or included within) the user terminal 108. Examples of the input device may include, but are not limited to, a keyboard, a mouse, a joy stick, a track pad, a voice-enabled input device, a touch-enabled input device, and/or a gesture-enabled input device.

In accordance with an embodiment, the UI manager 310 may be further configured to communicate with the UI manager 216, of the image-processing server 104, via the transceiver 304. Such communication may facilitate receipt of information that corresponds to the surgical scene interface. Thereafter, the UI manager 310 may present the surgical scene interface, via the UI of the user terminal 108.

The display adapter 312 may comprise suitable logic, circuitry, interfaces, and/or code that may be configured to interface the UI manager 310 with the display device 314. In accordance with an embodiment, the display adapter 312 may perform an adjustment of rendering and display properties of the UI of the user terminal 108, based on display configurations of the display device 314. Examples of one or more techniques that may be employed to perform the display adjustment may include, but are not limited to, image enhancement, image stabilization, contrast adjustment, brightness adjustment, resolution adjustment, and/or skew/rotation adjustment.

The display device 314 may comprise suitable logic, circuitry, interfaces, and/or code that may be configured to render the UI. In accordance with an embodiment, the display device 314 may be implemented as a part of the user terminal 108. In another embodiment, the display device 314 may be communicatively coupled to the user terminal 108. The display device 314 may be realized through several known technologies, such as Cathode Ray Tube (CRT) based display, Liquid Crystal Display (LCD), Light Emitting Diode (LED) based display, Organic LED display technology, Retina display technology, and/or the like. In addition, in accordance with an embodiment, the display device 314 may receive input from the user. In such a scenario, the display device 314 may be a touch screen that enables the user to provide the input. In accordance with an embodiment, the touch screen may correspond to at least one of a resistive touch screen, a capacitive touch screen, a thermal touch screen, and/or the like. In accordance with an embodiment, the display device 314 may receive the input through a virtual keypad, a stylus, a gesture-based input, and/or a touch-based input. In such a case, the input device may be integrated within the display device 314. Additionally, in accordance with an embodiment, the user terminal 108 may include a secondary input device apart from a touch-screen-based display device 314.

In operation, the transceiver 304 of the user terminal 108 may receive information that corresponds to the surgical scene interface from the UI manager 216, of the image-processing server 104, via the communication network 110. Thereafter, in accordance with an embodiment, the UI manager 310 of the user terminal 108 may present the surgical scene interface to the user, via the UI of the user terminal 108. In accordance with an embodiment, the surgical scene interface may present to the user one or more video frames, which may include the current video frame. In accordance with an embodiment, the one or more surgical tools localized in the current video frame may be masked or highlighted when the current video frame is displayed to the user. An example of the surgical scene interface is explained in more detail in FIG. 8.

In accordance with an embodiment, the one or more video frames presented by the surgical scene interface may be real-time video footage captured by the image-capturing device while the surgical or diagnostic procedure is performed. In such a case, the image-processing server 104 may analyze the one or more video frames on a real-time basis (online processing) to localize the one or more surgical tools present in the current video frame from the one or more video frames. The one or more surgical tools that may be localized in the current video frame may be simultaneously presented to the user as a masked or highlighted region in the current video frame, via the surgical scene interface.

In accordance with an embodiment, the surgical scene interface may be further configured to present a notification to the user to indicate the localization of the one or more surgical tools present in the current video frame. The notification may also indicate an extent and/or type of occlusion of each surgical tool in the current video frame. Examples of the notification may include, but are not limited to, an audio alert, a textual alert, a visual alert, and/or a haptic alert. The user (such as the physician) may be prompted to take an action based on the notification. For instance, the surgical scene interface may prompt the user to adjust the one or more image-capture settings of the image-capturing device. In accordance with an embodiment, the camera control unit 218 of the image-processing server 104 may be configured to determine optimal values for the one or more image-capture settings, based on the localization of the one or more surgical tools. The surgical scene interface may present these optimal values to the user as suggested values for the one or more image-capture settings. The user may adjust the one or more image-capture settings of the image-capturing device, based on the suggested values presented to the user. In addition to adjustment of the one or more image-capture settings of the image-capturing device, the user (such as the physician) may re-align/re-position the one or more surgical tools within the anatomical region to reduce an extent of occlusion of the one or more surgical tools.

Figure 4:
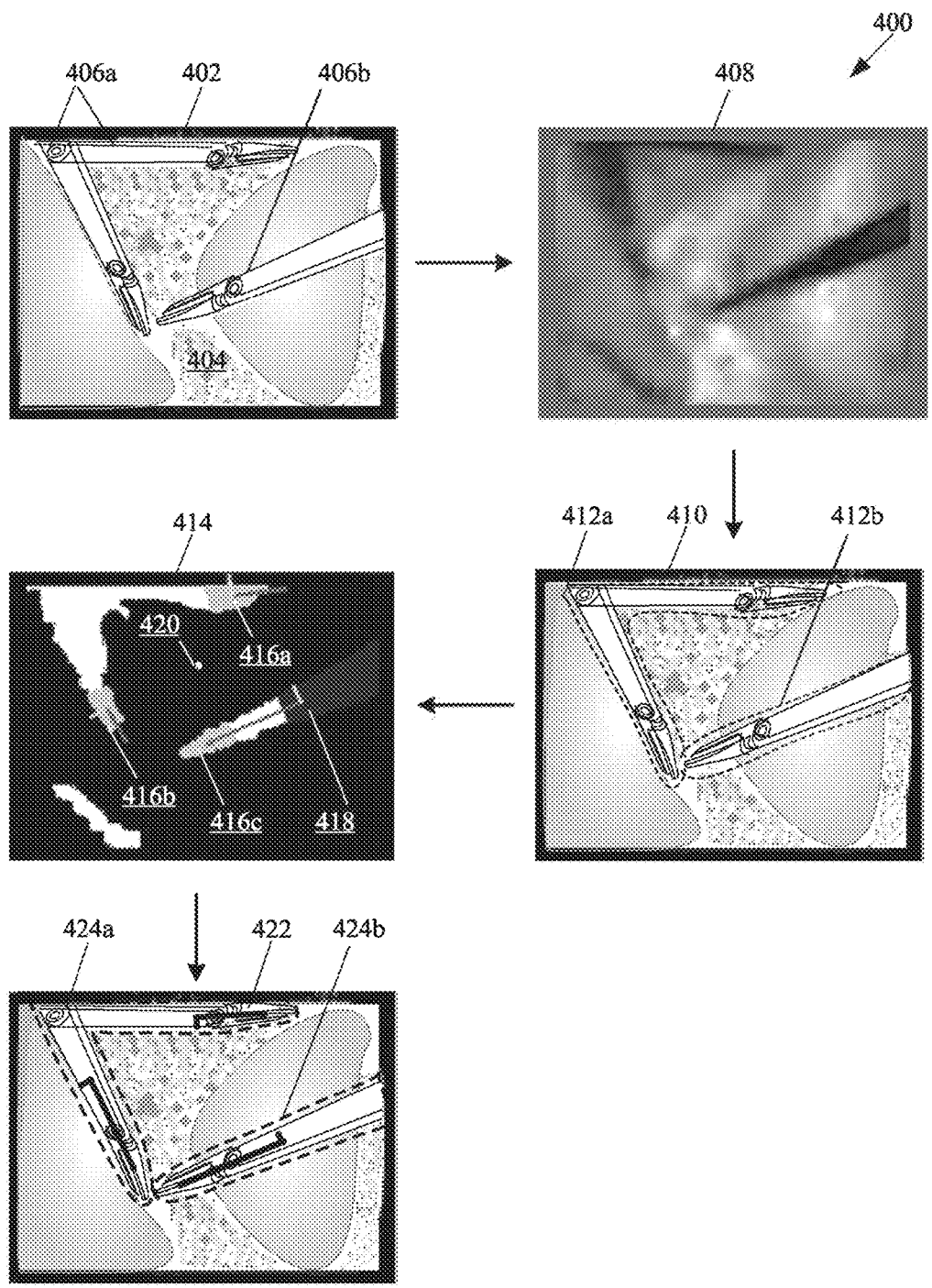
FIG. 4 illustrates an exemplary flow diagram of a method to estimate poses of one or more surgical tools in a video frame, in accordance with an embodiment of the disclosure.

FIG. 4 illustrates an exemplary flow diagram of a method to estimate poses of one or more surgical tools in a video frame, in accordance with an embodiment of the disclosure. FIG. 4 has been described in conjunction with elements from FIGS. 1 and 2. With reference to FIG. 4, there is shown a flow diagram 400. The flow diagram 400 comprises an input video frame 402, an anatomical region 404, a first surgical tool 406a, a second surgical tool 406b, a color/geometric-filtered video frame 408, a masked video frame 410, a first 2D mask 412a, and a second 2D mask 412b. The flow diagram 400 further comprises a preliminary pose-estimated video frame 414, a first tip 416a, a second tip 416b, a third tip 416c, a first end 418, a centroid 420, an output video frame 422, a first pose 424a, and a second pose 424b.

As shown in the flow diagram 400, the input video frame 402 illustrates a snapshot of a video frame from the one or more video frames captured by the image-capturing device. The input video frame 402 depicts the anatomical region 404, on which a surgical or diagnostic procedure is performed by use of the first surgical tool 406a and the second surgical tool 406b. In accordance with an embodiment, the image-filtering engine 210 of the image-processing server 104 may remove one or more smoke blocks from the input video frame 402, to generate a smoke-free video frame (not shown), if the input video frame 402 is occluded with the one or more smoke blocks. An exemplary flow diagram that illustrates a method to remove the one or more smoke blocks from the input video frame 402 to generate the smoke-free video frame is explained in conjunction with FIG. 5.

In accordance with an embodiment, the image-filtering engine 210 may be configured to analyze the input video frame 402 (or the smoke-free video frame) to determine one or more physical characteristics of the one or more surgical tools (such as the first surgical tool 406a and the second surgical tool 406b) in the input video frame 402. The determination of the one or more physical characteristics may be based on one or more color and geometric constraints. The one or more color constraints may correspond to an adaptive color filtering that may be performed based on the conditions, "Condition 1" and "Condition 2", as specified in FIG. 2. The image-filtering engine 210 may detect one or more regions of interest in the input video frame 402, which may correspond to the first surgical tool 406a and the second surgical tool 406b, based on the one or more color constraints. Further, the image-filtering engine 210 may apply the one or more geometric constraints on the determined one or more regions of interest to detect preliminary 2D masks of the one or more surgical tools (such as the first surgical tool 406a and the second surgical tool 406b) in the input video frame 402. As discussed earlier, the one or more geometric constraints may correspond to the determination of whether each region of interest satisfies a size, number of edges, and/or orientation condition. The regions of interest that satisfy the aforementioned conditions may be designated as parts of the preliminary 2D masks. The color/geometric-filtered video frame 408 illustrates a resultant video frame that may be obtained based on the application of the one or more color and geometric constraints on the input video frame 402 (or the smoke-free video frame).

In accordance with an embodiment, the image-filtering engine 210 may be configured to refine the preliminary 2D masks detected based on the one or more color and geometric constraints. The image-filtering engine 210 may determine contours in the preliminary 2D masks and then perform contour evolution on the determined contours. The contour evolution may be performed based on color characteristics of the first surgical tool 406a and the second surgical tool 406b by use of a level-set based technique, as specified in the equations (3) and (4) in FIG. 2. In accordance with an embodiment, the contour evolution may be based on a curvature and an intensity variance of regions inside and/or outside the contours of the preliminary 2D masks. The image-filtering engine 210 may obtain a contour-evolved video frame (not shown) based on the contour evolution.

Thereafter, the image-filtering engine 210 may perform segmentation on the contour-evolved video frame (not shown) to obtain a tool-segmented video frame (not shown). The tool-segmented video frame may include the refined 2D masks of the one or more surgical tools (such as the first surgical tool 406a and the second surgical tool 406b). An exemplary flow diagram that illustrates a method to refine the preliminary 2D masks of the one or more surgical tools (such as the first surgical tool 406a and the second surgical tool 406b) in the input video frame 402 is explained in FIG. 6. The masked video frame 410 illustrates a resultant video frame that may be obtained when the tool-segmented video frame (not shown) is overlaid over the input video frame 402. As shown in FIG. 4, the masked video frame 410 includes the first 2D mask 412a and the second 2D mask 412b. The first 2D mask 412a may correspond to a 2D mask that encompasses the first surgical tool 406a, while the second 2D mask 412b may correspond to a 2D mask that encompasses the second surgical tool 406b.

In accordance with an embodiment, the tool localizing engine 212 of the image-processing server 104 may be configured to estimate poses of the one or more surgical tools (such as the first surgical tool 406a and the second surgical tool 406b) from the masked video frame 410. The tool localizing engine 212 may estimate locations of tips and/or ends of the first surgical tool 406a and the second surgical tool 406b, based on an analysis of the first 2D mask 412a and the second 2D mask 412b, respectively. Thereafter, the tool localizing engine 212 may determine a location of a centroid of the locations of the tips and/or ends of the one or more surgical tools (such as the first surgical tool 406a and the second surgical tool 406b). For instance, the tool localizing engine 212 may estimate the locations of the first tip 416a and the second tip 416b, based on the first 2D mask 412a of the first surgical tool 406a. Further, the tool localizing engine 212 may estimate the locations of the third tip 416c and the first end 418, based on the second 2D mask 412b of the second surgical tool 406b. The tool localizing engine 212 may then determine the location of the centroid 420, based on the locations of the first tip 416a, the second tip 416b, the third tip 416c, and the first end 418. The preliminary pose-estimated video frame 414 illustrates a resultant video frame that may be obtained when the locations of the tips (such as the first tip 416a, the second tip 416b, and the third tip 416c), ends (such as the first end 418), and centroid (such as the centroid 420) are estimated from the masked video frame 410.

In accordance with an embodiment, the tool localizing engine 212 may further analyze the preliminary pose-estimated video frame 414 to determine whether the tips (such as the first tip 416a, the second tip 416b, and the third tip 416c), the ends (such as the first end 418), and/or the centroid (such as the centroid 420) is/are occluded. Further, the tool localizing engine 212 may determine whether the centroid (such as 420) lies outside the 2D masks (such as the first 2D mask 412a and the second 2D mask 412b). In accordance with an embodiment, the tool localizing engine 212 may re-estimate the locations of the tips (such as the first tip 416a, the second tip 416b, and the third tip 416c) and/or ends (such as the first end 418), if the centroid (such as the centroid 420) lies outside the 2D masks (such as the first 2D mask 412a and the second 2D mask 412b) or the centroid (such as the centroid 420) is occluded.

The tool localizing engine 212 may then update the location of the centroid (such as the centroid 420) based on the re-estimation of the locations of the tips (such as the first tip 416a, the second tip 416b, and the third tip 416c) and/or the ends (such as the first end 418). In accordance with an embodiment, the tool localizing engine 212 may estimate the poses of the one or more surgical tools (such as the first surgical tool 406a and the second surgical tool 406b) based on the estimated locations of the tips (such as the first tip 416a, the second tip 416b, and the third tip 416c), the ends (such as the first end 418), and the centroid (such as the centroid 420). The estimation of the poses may be based on the location of the ends (such as the first end 418), when the tips (such as the first tip 416a, the second tip 416b, and the third tip 416c) are occluded.

Further, the estimation of the poses may be based on the location of the tips (such as the first tip 416a, the second tip 416b, and the third tip 416c), when the ends (such as the first end 418) and/or the centroid (such as the centroid 420) is/are occluded. The estimation of the poses of the one or more surgical tools (such as the first surgical tool 406a and the second surgical tool 406b) is explained further with reference to the exemplary poses illustrated in FIGS. 7A to 7D. The output video frame 422 corresponds to a resultant video frame that may be obtained based on the estimation of the poses of the one or more surgical tools (such as the first surgical tool 406a and the second surgical tool 406b) from the preliminary pose-estimated video frame 414.

As shown in FIG. 4, the output video frame 422 may include the first pose 424a and the second pose 424b that respectively correspond to the poses estimated for the first surgical tool 406a and the second surgical tool 406b in the input video frame 402. The first principal axis and the second principal axis of the first surgical tool 406a are depicted within the first pose 424a. Further, the first and the second principal axes of the second surgical tool 406b are depicted within second pose 424b.

Figure 5:
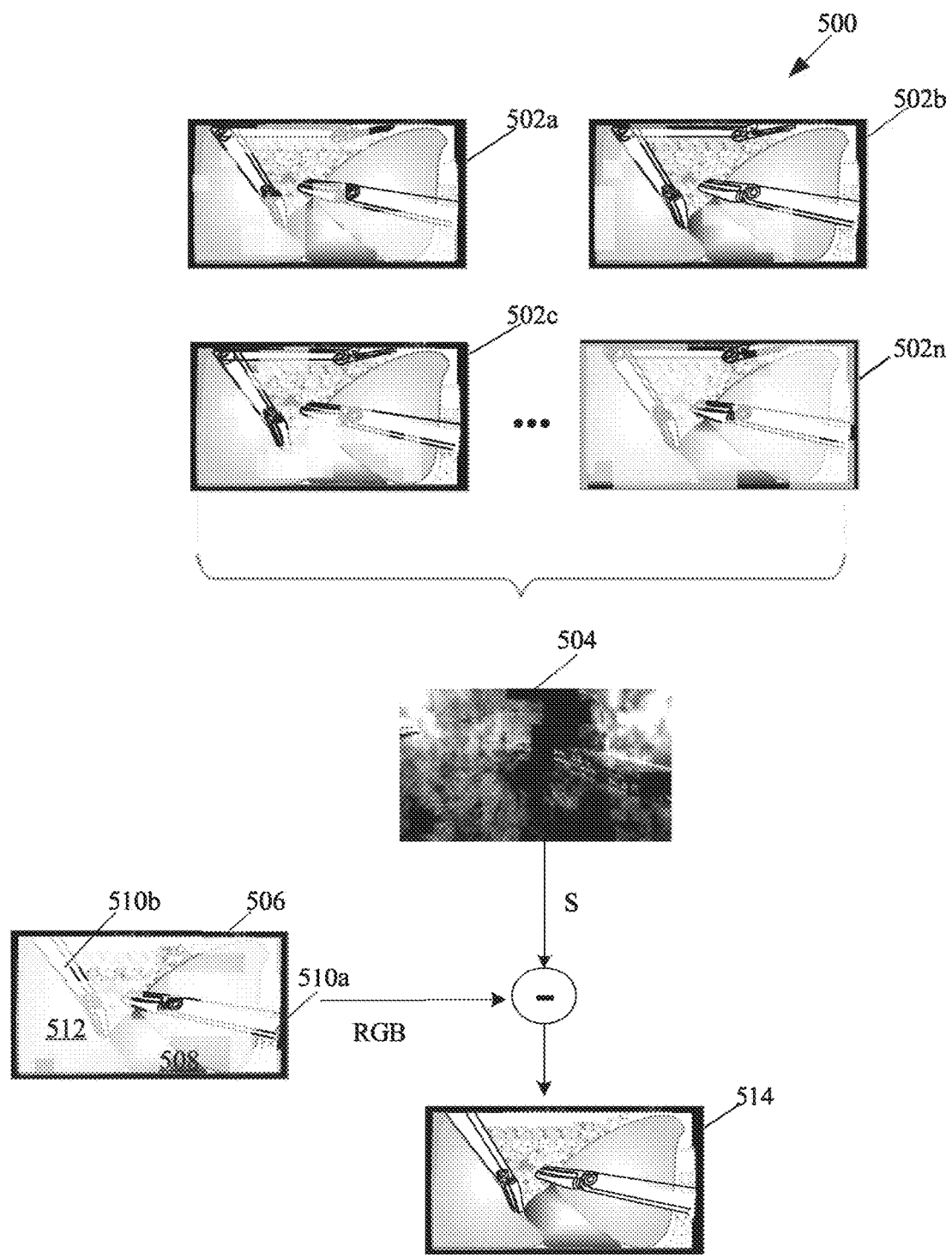
FIG. 5 illustrates an exemplary flow diagram of a method to remove one or more smoke blocks from a video frame, in accordance with an embodiment of the disclosure.

FIG. 5 illustrates an exemplary flow diagram of a method to remove one or more smoke blocks from a video frame, in accordance with an embodiment of the disclosure. FIG. 5 has been described in conjunction with elements from FIGS. 1 and 2. With reference to FIG. 5, there is shown a flow diagram 500. The flow diagram 500 comprises a set of previous video frames 502 that includes the video frames 502a to 502n. The flow diagram 500 further comprises an accumulated-smoke video frame 504, a current video frame 506, an anatomical region 508, a first surgical tool 510a and a second surgical tool 510b, one or more smoke blocks 512, and a smoke-free video frame 514.

In accordance with an embodiment, the current video frame 506 may correspond to a video frame from the one or more video frames captured by the image-capturing device. Further, the set of previous video frames 502 may correspond to video frames that may be captured by the image-capturing device, prior to the capture of the current video frame 506. Hence, the set of previous video frames 502 may occur chronologically before the current video frame 506, in the sequence of the one or more video frames captured by the image-capturing device.

In accordance with an embodiment, the image-filtering engine 210 of the image-processing server 104 may sequentially analyze a predetermined number of video frames that are captured prior to the current video frame 506 (such as the set of previous video frames 502). Based on the analysis of the prior video frames (such as the set of previous video frames 502), the image-filtering engine 210 may detect one or more smoke regions in each prior video frame (such as 502a to 502n). The image-filtering engine 210 may then determine an accumulated intensity of a set of pixels encompassed within each of the one or more smoke regions in each prior video frame (such as 502a to 502n). The image-filtering engine 210 may generate the accumulated-smoke video frame 504 to represent the accumulated intensity of the set of pixels in the one or more smoke regions detected from each prior video frame (such as 502a to 502n).

As shown in the flow diagram 500, the current video frame 506 depicts the anatomical region 508, on which a surgical or diagnostic procedure is performed by use of the first surgical tool 510a and the second surgical tool 510b. Further, the current video frame 506 may be occluded with smoke encompassed within one or more blocks (such as the one or more smoke blocks 512). In accordance with an embodiment, the image-filtering engine 210 may remove the one or more smoke blocks 512 from the current video frame 506, to generate the smoke-free video frame 514. In accordance with an embodiment, the image-filtering engine 210 may not remove a smoke block (of the one or more smoke blocks 512) from the current video frame 506, when an average intensity of pixels in that smoke block lies within a predetermined threshold.

In accordance with an embodiment, the removal of the one or more smoke blocks 512 from the current video frame 506 may be based on the accumulated-smoke video frame 504. For instance, the image-filtering engine 210 may subtract the intensity of pixels in the accumulated-smoke video frame 504 from intensity of corresponding pixels in the current video frame 506 to generate the smoke-free video frame 514.

Figure 6:
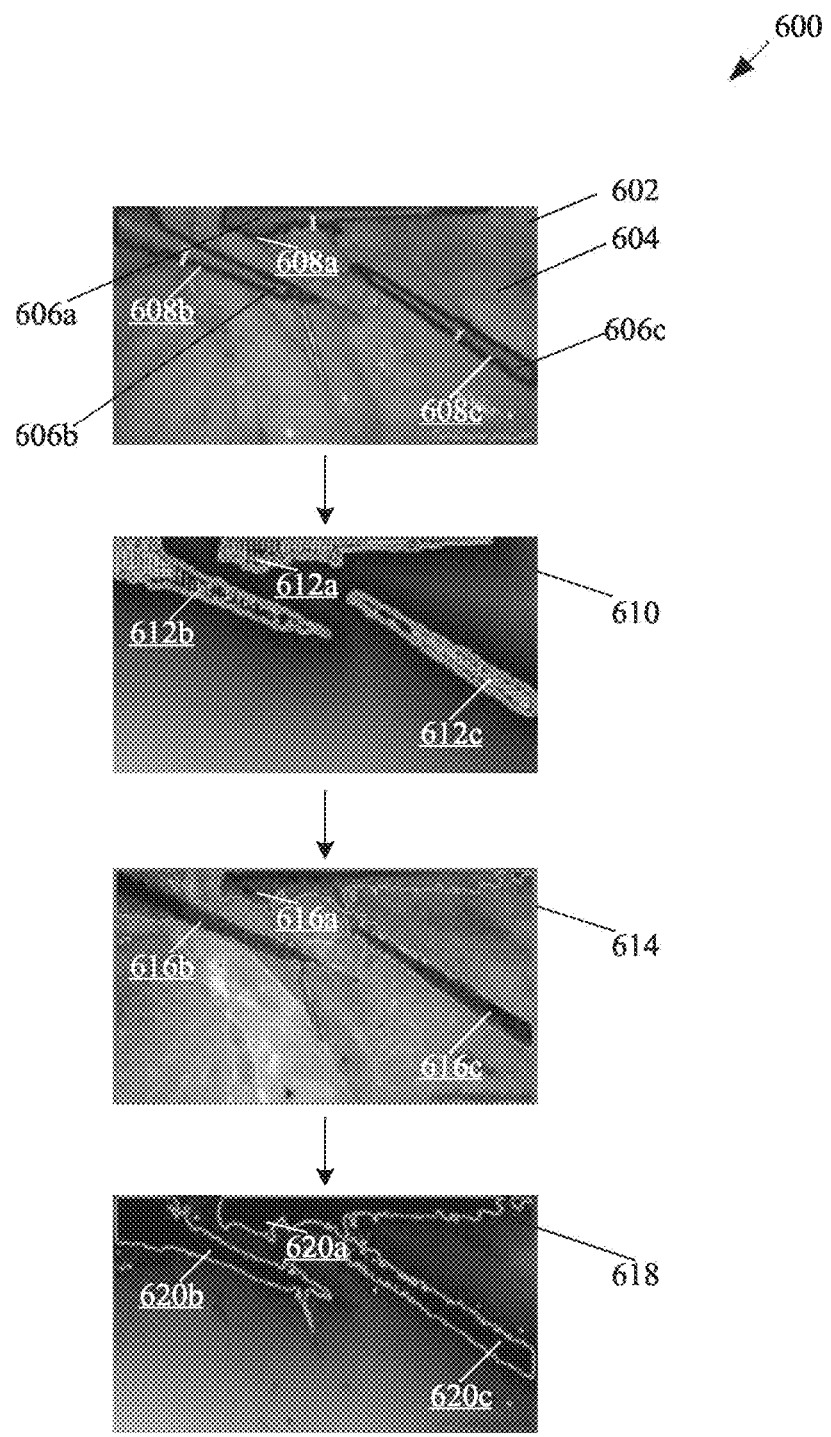
FIG. 6 illustrates an exemplary flow diagram of a method to refine preliminary two-dimensional (2D) masks of one or more surgical tools in a video frame, in accordance with an embodiment of the disclosure.

FIG. 6 illustrates an exemplary flow diagram of a method to refine preliminary 2D masks of one or more surgical tools in a video frame, in accordance with an embodiment of the disclosure. FIG. 6 has been described in conjunction with elements from FIGS. 1 and 2. With reference to FIG. 6, there is shown a flow diagram 600. The flow diagram 600 comprises a pre-processed video frame 602, an anatomical region 604, one or more surgical tools (such as a first surgical tool 606a, a second surgical tool 606b, and a third surgical tool 606c), and one or more 2D masks (such as a first 2D mask 608a, a second 2D mask 608b, and a third 2D mask 608c). Further, the flow diagram 600 comprises a contoured video frame 610, one or more tool contours (such as a first tool contour 612a, a second tool contour 612b, and a third tool contour 612c), a contour-evolved video frame 614, and one or more evolved-contours (such as a first evolved contour 616a, a second evolved contour 616b, and a third evolved contour 616c). The flow diagram 600 additionally includes a tool-segmented video frame 618 and one or more tools segments (such as a first tool segment 620a, a second tool segment 620b, and a third tool segment 620c).

In accordance with an embodiment, the image-filtering engine 210 of the image-processing server 104 may perform a preliminary analysis of a current video frame (not shown) from the one or more video frames captured by the image-capturing device. Based on the preliminary analysis, the image-filtering engine 210 may detect preliminary 2D masks of the one or more surgical tools (such as 606a, 606b, and 606c) in the current video frame, as discussed earlier in FIG. 4. The pre-processed video frame 602 illustrates a resultant video frame that may be generated from the current video frame (not shown), based on the preliminary analysis. The pre-processed video frame 602 may include the preliminary 2D masks that may be detected in the current video frame, such as the first 2D mask 608a, the second 2D mask 608b, and the third 2D mask 608c. The pre-processed video frame 602 further includes the first surgical tool 606a, the second surgical tool 606b, and the third surgical tool 606c. The first 2D mask 608a may encompass the first surgical tool 606a, while the second 2D mask 608b may encompass the second surgical tool 606b. Further, the third surgical tool 606c may be encompassed within the third 2D mask 608c.

In accordance with an embodiment, the image-filtering engine 210 may be configured to determine contours of the detected preliminary 2D masks (such as 608a, 608b, and 608c) from the pre-processed video frame 602. The contoured video frame 610 illustrates a resultant video frame that may be generated from the pre-processed video frame 602, based on the determination of the contours of the detected preliminary 2D masks (such as the first 2D mask 608a, the second 2D mask 608b, and the third 2D mask 608c). The contoured video frame 610 may include the determined contours, such as the first tool contour 612a, the second tool contour 612b, and the third tool contour 612c. The first tool contour 612a may correspond to the first 2D mask 608a (of the first surgical tool 606a), while the second tool contour 612b may correspond to the second 2D mask 608b (of the second surgical tool 606b). Further, the third tool contour 612c may correspond to the third 2D mask 608c (of the third surgical tool 606c).

In accordance with an embodiment, the image-filtering engine 210 may be further configured to perform contour evolution on the determined contours (such as the first tool contour 612a, the second tool contour 612b, and the third tool contour 612c) in the contoured video frame 610. The contour evolution may be performed based on color characteristics of the one or more surgical tools (such as the first surgical tool 606a, the second surgical tool 606b, and the third surgical tool 606c), by use of a level-set based technique, as specified in equations (3) and (4), as specified in FIG. 2. In accordance with an embodiment, the contour evolution may be based on a curvature and an intensity variance of regions inside and/or outside the contours (such as the first tool contour 612a, the second tool contour 612b, and the third tool contour 612c). The contour-evolved video frame 614 illustrates a resultant video frame that may be obtained from the contoured video frame 610, based on the performance of the contour evolution on the contours (such as the first tool contour 612a, the second tool contour 612b, and the third tool contour 612c). The contour-evolved video frame 614 may include the one or more evolved contours, such as the first evolved contour 616a, the second evolved contour 616b, and the third evolved contour 616c. The first evolved contour 616a may correspond to the first tool contour 612a, while the second evolved contour 616b may correspond to the second tool contour 612b. Further, the third evolved contour 616c may correspond to the third tool contour 612c.

In accordance with an embodiment, the image-filtering engine 210 may be further configured to perform segmentation of contour-evolved video frame 614 to obtain the tool-segmented video frame 618. The tool-segmented video frame 618 may include one or more tool segments, such as the first tool segment 620a, the second tool segment 620b, and third tool segment 620c. The first tool segment 620a may be determined based on the segmentation of the first evolved contour 616a. Further, the second tool segment 620b and the third tool segment 620c may be respectively determined based on the segmentation of the second evolved contour 616b and the third evolved contour 616c. In accordance with an embodiment, image-filtering engine 210 may refine the preliminary 2D masks (such as the first 2D mask 608a, the second 2D mask 608b, and the third 2D mask 608c) of the one or more surgical tools (such as the first surgical tool 606a, the second surgical tool 606b, and the third surgical tool 606c). The refinement may be based on the one or more tool segments (such as the first tool segment 620a, the second tool segment 620b, and third tool segment 620c).

Figure 7A:
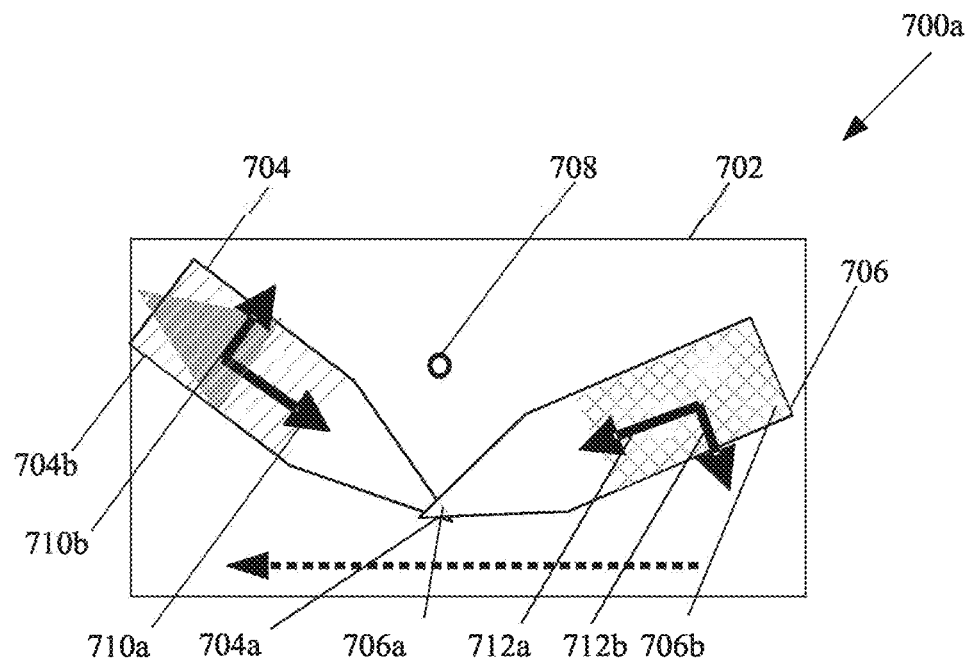
FIGS. 7A to 7D illustrate exemplary scenarios of poses of one or more surgical tools in a video frame, in accordance with an embodiment of the disclosure.
Figure 7B:
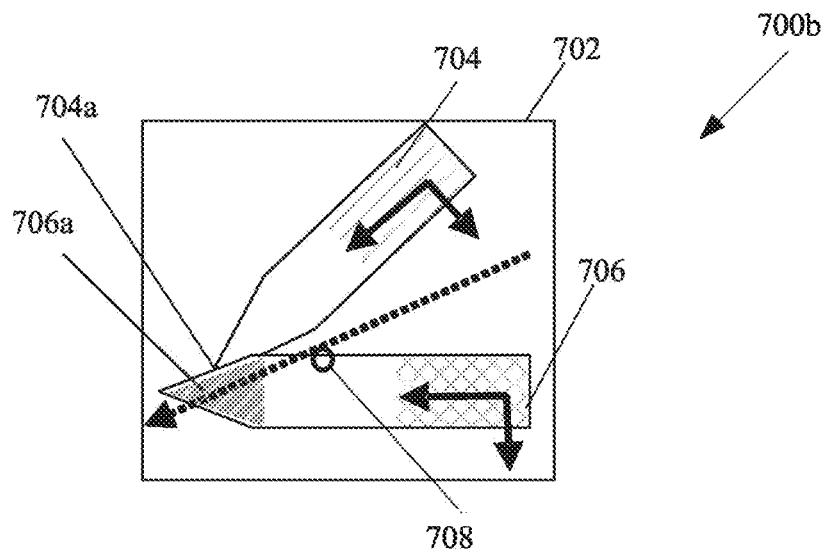
Figure 7C:
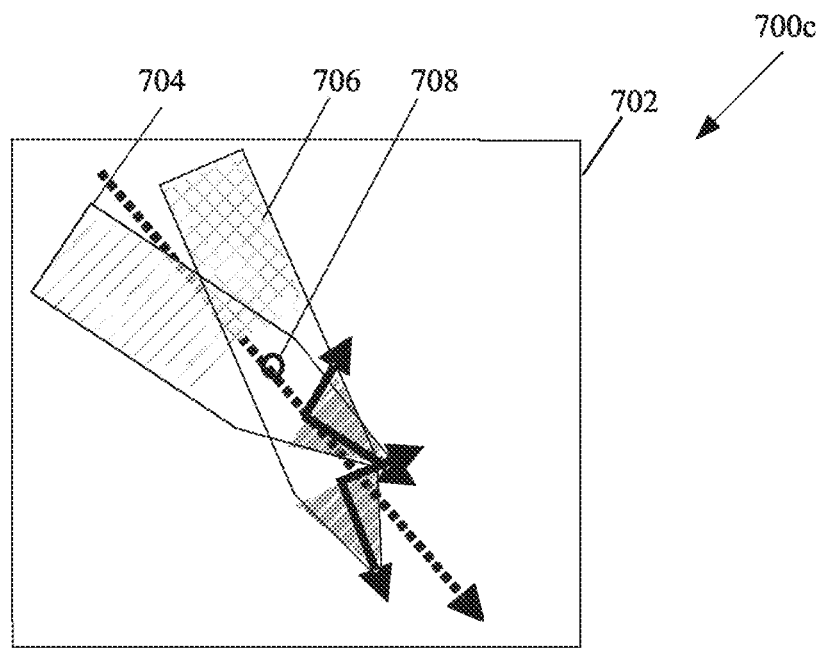
Figure 7D:
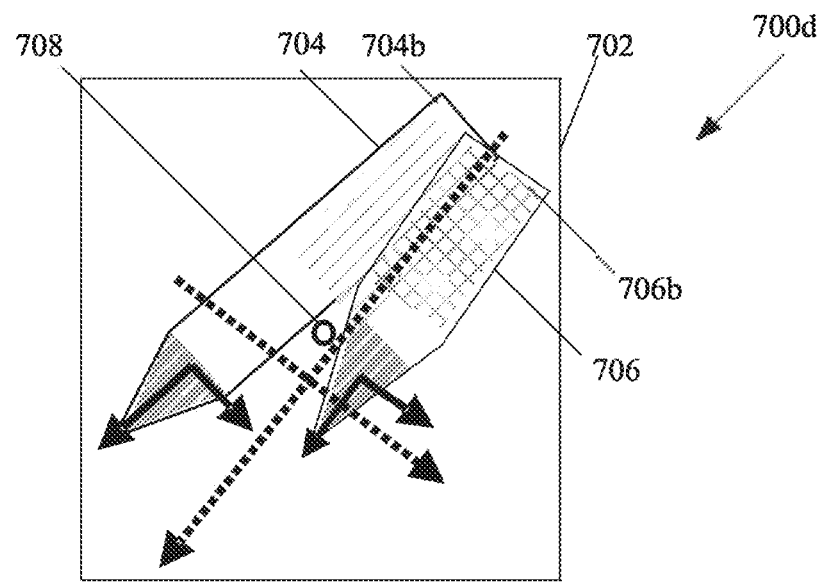

FIGS. 7A to 7D illustrate exemplary scenarios of poses of one or more surgical tools in a video frame, in accordance with an embodiment of the disclosure. With reference to FIG. 7A, there is shown a first exemplary scenario 700a. Further, FIG. 7B depicts a second exemplary scenario 700b, while FIGS. 7C and 7D depict a third exemplary scenario 700c and a fourth exemplary scenario 700d, respectively. Each of the four exemplary scenarios (such as 700a to 700d) depicts a video frame 702 that includes a first surgical tool 704 and a second surgical tool 706. However, poses of the surgical tools 704 and 706, differ in the four exemplary scenarios, 700a to 700d.

The first exemplary scenario 700a depicts occlusion at a tip (depicted by 704a) of the first surgical tool 704, while the second exemplary scenario 700b depicts occlusion at a tip (depicted by 706a) of the second surgical tool 706. In addition, the third exemplary scenario 700c depicts occlusion at a centroid of the tips and ends (depicted by 708) of the two surgical tools. Further, the fourth exemplary scenario 700d depicts occlusion at an end (depicted by 704b) of the first surgical tool 704. Each exemplary scenario (such as 700a to 700d) further depicts a first set of principal axes (that include principal axes 710a and 712a) and a second set of principal axes (that include principal axes 710b and 712b). The principal axes 710a and 710b may respectively correspond to a first principal axis and a second principal axis of the first surgical tool 704. Further, the principal axes 712a and 712b may respectively correspond to a first principal axis and a second principal axis of the second surgical tool 706. In accordance with an embodiment, each of the second set of principal axes may be at a predetermined angle with respect to an associated principal axes from the first set of principal axes. For instance, the principal axes 710a and 710b (of the first surgical tool 704) may be orthogonal to each other. Similarly, the principal axes 712a and 712b (of the second surgical tool 706) may also be orthogonal to each other.

In accordance with an embodiment, the tool localizing engine 212 of the image-processing server 104 may estimate locations of the tips and/or ends of one or more surgical tools (such as the first surgical tool 704 and the second surgical tool 706) in the video frame 702. The locations of the tips and/or ends may be estimated based on an analysis of 2D masks of the one or more surgical tools (such as the first surgical tool 704 and the second surgical tool 706) detected in the video frame 702. The detection of the 2D masks is explained in detail in FIG. 2 and FIG. 4.

In accordance with an embodiment, the tool localizing engine 212 may analyze the 2D masks along a first principal axis (such as a latitudinal principal axis) to estimate the locations of the tips and/or ends. For instance, the tool localizing engine 212 may analyze the 2D mask of the first surgical tool 704 along the first principal axis, such as 710*a*, of the first surgical tool 704. Further, the tool localizing engine 212 may analyze the 2D mask of the second surgical tool 706 along the first principal axis, such as 710*b*, of the second surgical tool 706. The tool localizing engine 212 may determine location of a centroid of the tips and/or ends based on the location.

In accordance with an embodiment, when the centroid is occluded or the centroid lies outside the detected 2D masks, the tool localizing engine 212 may re-estimate the locations of the tips and/or ends of the one or more surgical tools (such as the first surgical tool 704 and the second surgical tool 706). For instance, the centroid may lie outside the detected 2D masks in the first exemplary scenario 700*a* and the fourth exemplary scenario 700*d*, while the centroid may be occluded in the third exemplary scenario 700*c*. Hence, the tool localizing engine 212 may re-estimate the locations of the tips and/or ends of the one or more surgical tools (such as the first surgical tool 704 and the second surgical tool 706) in case of the first, third, and fourth exemplary scenarios, such as 700*a*, 700*c*, and 700*d*, respectively.

Further, the tool localizing engine 212 may update the location of the centroid based on the re-estimated locations of the tips and/or ends. The re-estimation of the locations of the tips and/or ends may be based on an analysis of the detected 2D masks along a second principal axis (such as the second principal axis 710*b* of the first surgical tool 704 and the second principal axis 712*b* of the second surgical tool 706). The second principal axis may be at a predetermined angle with respect to the first principal axis. For instance, the second principal axis may be orthogonal to the first principal axis. Hence, if the first principal axis corresponds to a latitudinal principal axis of the detected 2D mask, the second principal axis may correspond to a longitudinal principal axis of the detected 2D mask. In accordance with an embodiment, the tool localizing engine 212 may estimate the poses of the one or more surgical tools (such as the first surgical tool 704 and the second surgical tool 706) in the video frame 702, based on the estimated locations of the tips and/or ends.

The first exemplary scenario 700*a* of FIG. 7A illustrates a scenario where the tip (depicted by 704*a*) of the first surgical tool 704 is occluded by the tip of the second surgical tool 706 (depicted by 706*a*) at an obtuse angle (greater than "90 degrees" and less than "180 degrees"). The tool localizing engine 212 may analyze the 2D mask of the first surgical tool 704 and the second surgical tool 706 along the first principal axes (denoted by 710*a* and 712*a*) of the respective surgical tools. Here, the number of non-occluded tips and the number of non-occluded ends of the first surgical tool 704 and the second surgical tool 706 are equal to one. Based on the analysis of the 2D masks along the first principal axes, the tool localizing engine 212 may determine that the centroid of the tips and ends (depicted by 708) lies outside the 2D masks. Hence, the tool localizing engine 212 may ascertain that one or more of the tips may be occluded. To estimate the poses of the surgical tools 704 and 706, the tool localizing engine 212 may further analyze the 2D masks of these tools along the second principal axes (denoted by 710*b* and 712*b*) of the respective surgical tools. In this case, the estimation of the poses of the first surgical tool 704 and the second surgical tool 706, may be based on the estimated locations of the respective ends of the first surgical tool 704 and the second surgical tool 706, respectively.

The second exemplary scenario 700*b* of FIG. 7B illustrates a scenario where the tip (depicted by 706*a*) of the second surgical tool 706 is occluded by the tip (depicted by 704*a*) of the first surgical tool 704 at an acute angle (less than or equal to "90 degrees"). The tool localizing engine 212 may analyze the 2D masks of the surgical tools 704 and 706 along the first principal axes (denoted by 710*a* and 712*a*) of the respective surgical tools to detect the tips and ends of the surgical tools 704 and 706. Here, the number of non-occluded tips may be less than the number of non-occluded ends of the one or more surgical tools (such as the first surgical tool 704 and the second surgical tool 706). A person skilled in the art will appreciate that, in the current scenario, the tool localizing engine 212 need not analyze the 2D masks of the surgical tools 704 and 706 along their second principal axes (710*b* and 712*b* respectively), as the centroid of the tips and ends (depicted by 708) may lie inside the 2D masks. Further, in this scenario, the tool localizing engine 212 may estimate the poses of the first surgical tool 704 and the second surgical tool 706, based on the estimated locations of the respective ends of the first surgical tool 704 and the second surgical tool 706, respectively.

The third exemplary scenario 700*c* of FIG. 7C illustrates occlusion at a centroid (such as the occluded centroid 708) of the tips and/or ends of the first surgical tool 704 and the second surgical tool 706. The tool localizing engine 212 may analyze the 2D masks of the surgical tools 704 and 706 along the first principal axes (denoted by 710*a* and 712*a*) of the respective surgical tools to detect the tips and ends of the surgical tools 704 and 706. Here, the number of non-occluded tips may be greater than or equal to the number of non-occluded ends of the one or more surgical tools (such as the first surgical tool 704 and the second surgical tool 706). A person skilled in the art will appreciate that, in the current scenario, the tool localizing engine 212 need not analyze the 2D masks of the surgical tools 704 and 706 along their second principal axes (710*b* and 712*b* respectively), as the centroid of the tips and ends (depicted by 708) may lie inside the 2D masks. Further, in this scenario, the tool localizing engine 212 may estimate the poses of the first surgical tool 704 and the second surgical tool 706, based on the estimated locations of the respective tips of the first surgical tool 704 and the second surgical tool 706, respectively.

The fourth exemplary scenario 700*d* of FIG. 7D illustrates a scenario where the end (depicted by 704*b*) of the first surgical tool 704 is occluded by the end (depicted by 706*b*) of the second surgical tool 706. The tool localizing engine 212 may analyze the 2D masks of the surgical tools 704 and 706 along the first principal axes (denoted by 710*a* and 712*a*) of the respective surgical tools to detect the tips and ends of the surgical tools 704 and 706. Here, the number of non-occluded tips is greater than or equal to the number of non-occluded ends of the one or more surgical tools (such as the first surgical tool 704 and the second surgical tool 706). Based on the analysis of the 2D masks along the first principal axes, the tool localizing engine 212 may determine that the centroid of the tips and ends (depicted by 708) lies outside the 2D masks. Hence, the tool localizing engine 212 may ascertain that one or more of the ends may be occluded. To estimate the poses of the surgical tools 704 and 706, the tool localizing engine 212 may further analyze the 2D masks of these tools along the second principal axes (denoted by 710*b* and 712*b*) of the respective surgical tools. In this case, the tool localizing engine 212 may estimate the poses of the first surgical tool 704 and the second surgical tool 706, based on the estimated locations of the respective tips of the first surgical tool 704 and the second surgical tool 706, respectively.

Figure 8:
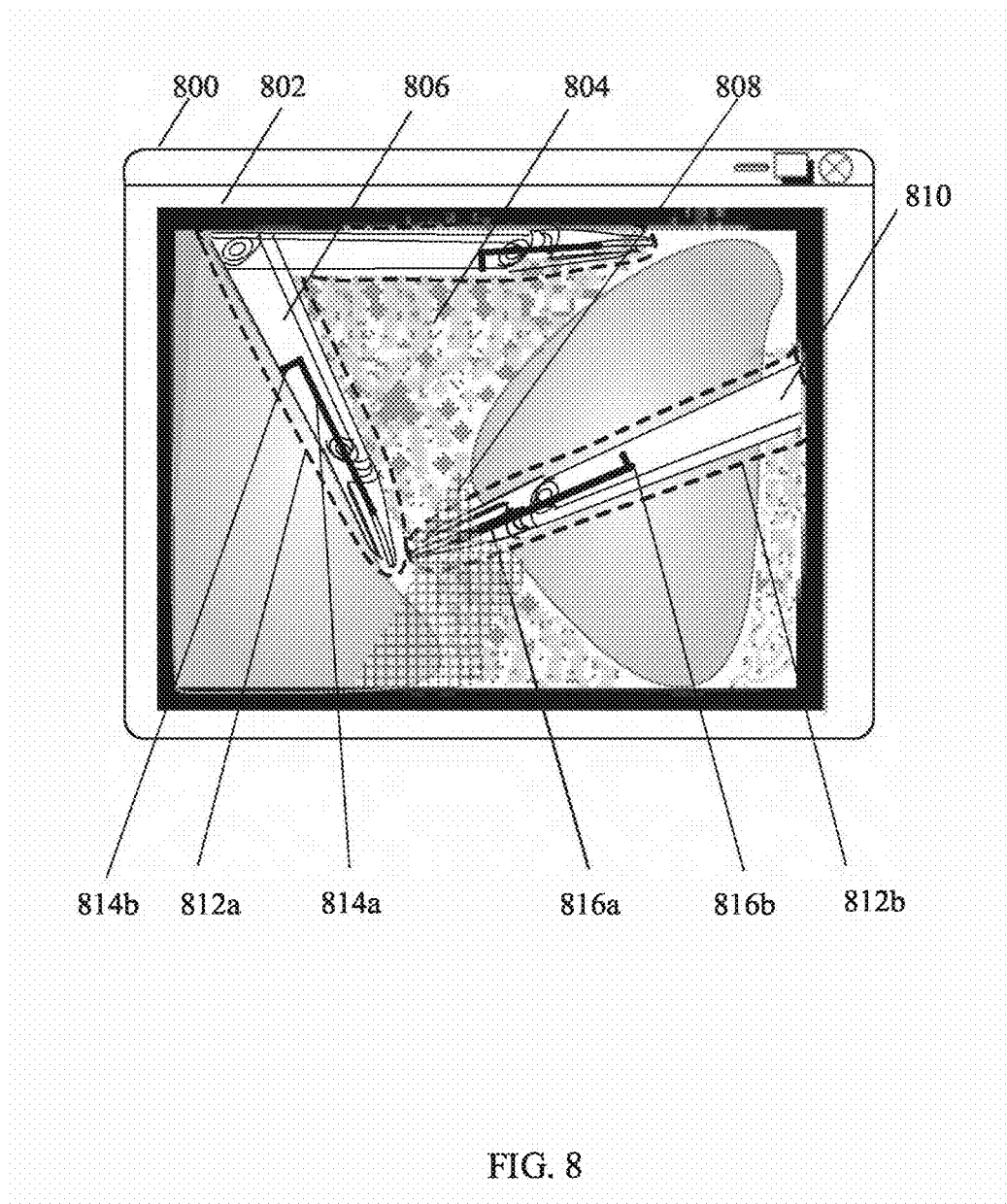
FIG. 8 illustrates an exemplary scenario of a user interface (UI) that may be presented on a user terminal, in accordance with an embodiment of the disclosure.

FIG. 8 illustrates an exemplary scenario of a UI that may be presented on the user terminal 108, in accordance with an embodiment of the disclosure. FIG. 8 has been described in conjunction with elements of FIG. 1. With reference to FIG. 8, there is shown a user interface (UI), which may be presented to a user of the user terminal 108.

In accordance with an embodiment, the UI may be configured to display a surgical scene interface 802 to present one or more video frames to the user. For instance, as shown in FIG. 8, the surgical scene interface 802 may display a video frame that includes a snapshot of a perspective cross-sectional view of an anatomical region 804 of a patient. The snapshot may be captured while a surgical or diagnostic procedure is performed on the anatomical region 804.

As illustrated in the snapshot, the surgical or diagnostic procedure may be performed by use of one or more surgical gauzes, such as a surgical gauze 808, and one or more surgical instruments, such as a surgical forceps 806 (a first surgical tool) and an endoscopic surgical instrument 810 (a second surgical tool). For instance, as shown in FIG. 8, a surface of the anatomical region 804 may be held by use of the surgical forceps 806, when the surgical or diagnostic procedure is performed by use of the endoscopic surgical instrument 810. Further, the surgical gauze 808 may be used to absorb blood or other body fluids that may ooze while the surgical or diagnostic procedure is performed. Although a single surgical gauze and two surgical instruments are shown in FIG. 8, one or more additional surgical gauzes and/or surgical instruments may also be used to perform the surgical or diagnostic procedure, without departure from the scope of the disclosure. As shown in FIG. 8, the surgical scene interface 802 further illustrates a first boundary 812*a* and a second boundary 812*b* that respectively encompass the surgical forceps 806 and the endoscopic surgical instrument 810 in the snapshot of the video frame. The surgical scene interface 802 further depicts a first pose axis (denoted by 814*a*) and a second pose axis (denoted by 814*b*) of the surgical forceps 806 within the first boundary 812*a*. In addition, the surgical scene interface 802 depicts a first and a second pose axes (denoted by 816*a* and 816*b*, respectively) of the endoscopic surgical instrument 810 within the second boundary 812*b*.

In operation, prior to the display of a particular video frame in the surgical scene interface 802, the image-processing server 104 may analyze the video frame. In accordance with an embodiment, the image-filtering engine 210 of the image-processing server 104 may determine one or more physical characteristics of one or more surgical tools (such as the surgical forceps 806 and the endoscopic surgical instrument 810) in the video frame. The determination of the one or more physical characteristics may be based on one or more color and geometric constraints. Thereafter, the image-filtering engine 210 may detect 2D masks of the one or more surgical tools (such as 806 and 810) present in the video frame, based on the determined one or more physical characteristics. Further, the tool localizing engine 212 of the image-processing server 104 may estimate poses of the one or more surgical tools (such as 806 and 810) in the video frame based on occlusion at tips and/or ends of the one or more surgical tools. The one or more surgical tools (such as 806 and 810) may be localized within the video frame based on the estimated poses of the respective surgical tools.

In accordance with an embodiment, the surgical scene interface 802 may mask or highlight the one or more surgical tools (such as 806 and 810) that may be localized in the video frame, while the video frame is presented to the user. For instance, the surgical scene interface 802 may display the first boundary 812*a* that encompasses the surgical forceps 806 in the video frame, based on the localization and pose estimation of the surgical forceps 806. Similarly, the surgical scene interface 802 may display the second boundary 812*b* that encompasses the endoscopic surgical instrument 810 in the video frame, based on the localization and pose estimation of the endoscopic surgical instrument 810. In accordance with an embodiment, the surgical scene interface 802 may display the first pose axis 814*a* and the second pose axis 814*b* of the surgical forceps 806 within the first boundary 812*a*, based on the estimation of the pose of the surgical forceps 806. Further, based on the estimation of the pose of the endoscopic surgical instrument 810, the surgical scene interface 802 may also display the first and the second pose axes (such as 816*a* and 816*b*, respectively) of the endoscopic surgical instrument 810.

In accordance with an embodiment, the surgical scene interface 802 may be further configured to present a notification to the user to indicate the localization of the one or more surgical tools (such as the surgical forceps 806 and the endoscopic surgical instrument 810) in the video frame. The notification may also indicate an extent and/or type of occlusion of each surgical tool (such as 806 and 810) in the video frame. Examples of the notification may include, but are not limited to, an audio alert, a textual alert, a visual alert, and/or a haptic alert. In case the video frame is presented in real time, the surgical scene interface 802 may prompt the user (such as the physician) to take a particular action based on the notification. For instance, the surgical scene interface 802 may prompt the user to adjust the one or more image-capture settings of the image-capturing device.

The surgical scene interface 802 may suggest optimal values for the one or more image-capture settings. The user may adjust the one or more image-capture settings of the image-capturing device, based on the suggested optimal values presented to the user. In addition to adjustment of the one or more image-capture settings of the image-capturing device, the user (such as the physician) may re-align/re-position the one or more surgical tools (such as 806 and 810) within the anatomical region 804 to reduce an extent of occlusion of the one or more surgical tools (such as 806 and 810). A person with ordinary skill in the art will understand that the UI in FIG. 8 has been provided for exemplary purposes and should not be construed to limit the scope of the disclosure.

Various embodiments of the disclosure may encompass numerous advantages. As discussed above, the image-processing server 104 may analyze the one or more video frames to localize one or more surgical tools in each video frame in real time, based on estimation of poses of the one or more surgical tools. During analysis of the video frame, the image-processing server 104 may initially determine one or more physical characteristics of one or more surgical tools, based on one or more color and geometric constraints. The image-processing server 104 may remove one or more smoke blocks from the video frame to generate a smoke-free video frame, when the video frame is occluded with the one or more smoke blocks. The removal of the one or more smoke blocks may improve an accuracy of the process of the localization of the one or more surgical tools. Further, the image-processing server 104 may detect 2D masks of the one or more surgical tools, based on the one or more physical characteristics and the removal of the one or more smoke blocks. As discussed, the image-processing server 104 may refine the detected 2D masks based on contour evolution of contours associated with the detected 2D masks of the one or more surgical tools. Thus, the initially detected 2D masks may thus be refined that may further improve detection of the one or more surgical tools in the video frame.

In accordance with an embodiment, the image-processing server 104 may be configured to estimate poses of the one or more surgical tools, based on the occlusion of tips/ends of the one or more surgical tools in the detected 2D masks of the one or more surgical tools. Such estimation of poses may be robust to occlusion of the tips and/or ends of the one or more surgical tools.

During the surgical or diagnostic procedure, the image-processing server 104 may provide a notification to a physician in real time that may indicate the localization of the one or more surgical tools in the video frame. The notification may further indicate an extent and/or type of occlusion of the one or more surgical tools. Based on the real-time notification, the physician may re-align/re-position the one or more surgical tools within the anatomical region to reduce an extent of occlusion of the one or more surgical tools while the surgical or diagnostic procedure is performed.

Further, as discussed, the image-processing server 104 may also enable the physician to adjust the one or more image-capture settings of the image-capturing device, based on the localization of the one or more surgical tools in a particular video frame. Such adjustment in the one or more image-capture settings may help in improvement of the quality of the one or more video frames captured by the image-capturing device in real time.

Figure 9:
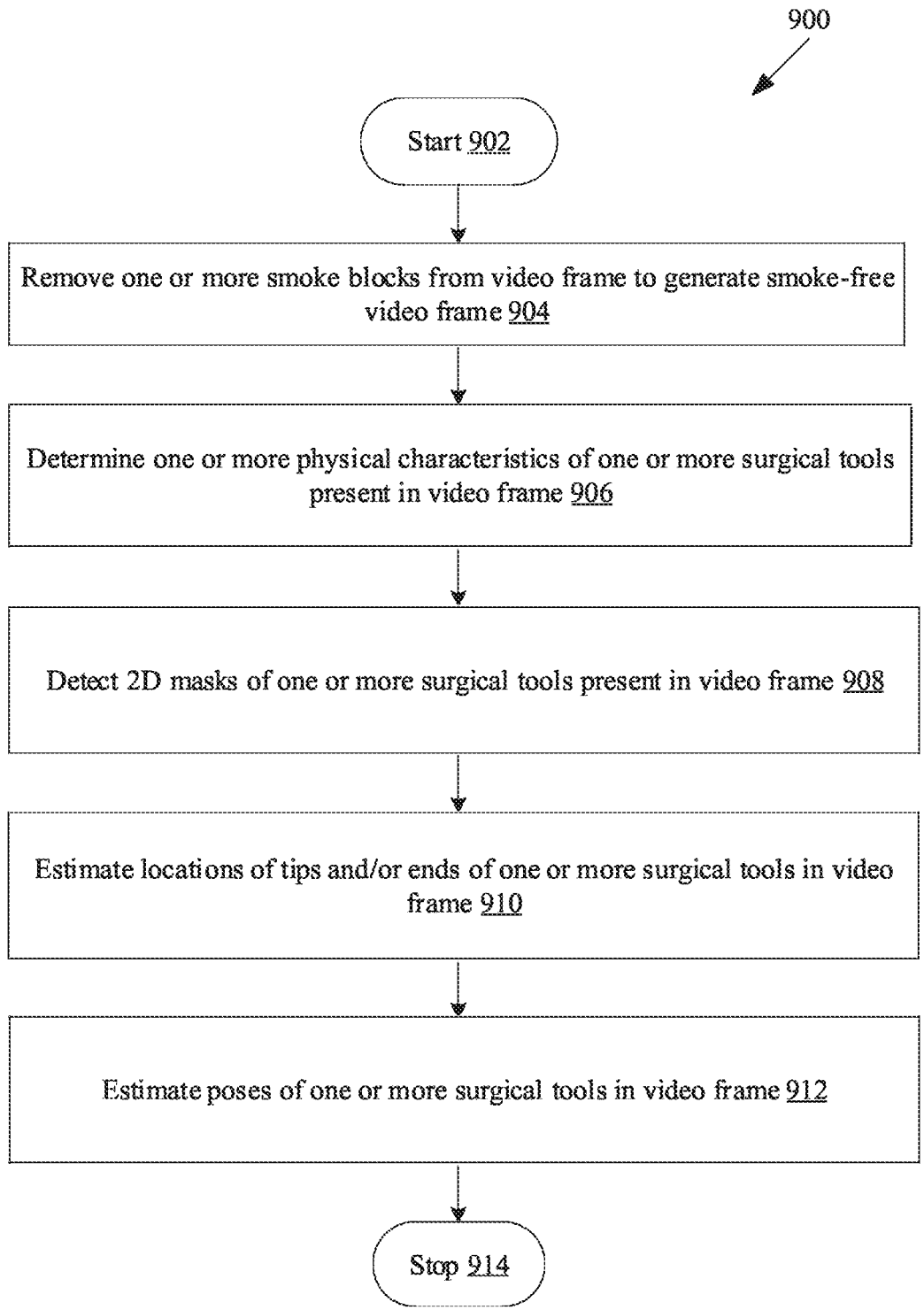
FIG. 9 is an exemplary flow chart that illustrates an exemplary method to localize surgical tools during anatomical surgery, in accordance with an embodiment of the disclosure.

FIG. 9 is an exemplary flow chart that illustrates an exemplary method to localize surgical tools during anatomical surgery, in accordance with an embodiment of the disclosure. With reference to FIG. 9, there is shown a flow chart 900. The flow chart 900 is described in conjunction with FIGS. 1 and 2. The method starts at step 902 and proceeds to step 904.

At step 904, one or more smoke blocks of the video frame may be removed from the video frame to generate a smoke-free video frame. In accordance with an embodiment, the image-filtering engine 210 may be configured to remove the one or more smoke blocks of the video frame to generate the smoke-free video frame, when the video frame is occluded with the one or more smoke blocks. In accordance with an embodiment, the image-filtering engine 210 may analyze a set of prior video frames (such as a predetermined number of video frames that occur temporally before the current video frame) to detect one or more smoke regions in each video frame from the set of prior video frames. The image-filtering engine 210 may determine an accumulated intensity of a set of pixels in the detected one or more smoke regions in the set of prior video frames. The removal of the one or more smoke blocks from the video frame may be based on the accumulated intensity of the set of pixels in the detected one or more smoke regions in the set of prior video frames.

At step 906, one or more physical characteristics of one or more surgical tools present in a video frame may be determined. In accordance with an embodiment, the image-filtering engine 210 of the image-processing server 104 may be configured to determine the one or more physical characteristics of the one or more surgical tools in the video frame (or the smoke-free video frame). In accordance with an embodiment, the one or more physical characteristics of the one or more surgical tools may be determined based on one or more color and geometric constraints. The one or more color and geometric constraints are specified with reference to FIG. 2.

At step 908, 2D masks of the one or more surgical tools present in the video frame may be detected. In accordance with an embodiment, the image-filtering engine 210 may be configured to detect the 2D masks of the one or more surgical tools, based on the determined one or more physical characteristics of the one or more surgical tools. The determination of the 2D masks of the one or more surgical tools is explained in detail in FIG. 2. In accordance with an embodiment, the image-filtering engine 210 may be further configured to refine the 2D masks of the one or more surgical tools based on contour evolution of contours associated with the initial 2D masks of the one or more tools. The refinement of the 2D masks of the one or more surgical tools is explained in detail in FIG. 6.

At step 910, locations of tips/ends of the one or more surgical tools in the video frame may be estimated. In accordance with an embodiment, the tool localizing engine 212 may be configured to estimate the locations of the tips and/or ends of the one or more surgical tools in the video frame. The estimation of the locations of the tips and/or ends may be based on an analysis of the detected 2D of the one or more surgical tools. Further, the tool localizing engine 212 may determine a location of the centroid of the tips and/or ends of the one or more tools. In accordance with an embodiment, the tool localizing engine 212 may re-estimate the locations of the tips and/or ends of the one or more surgical tools, when the centroid is occluded or the centroid lies outside the 2D masks of the one or more surgical tools. Further, the tool localizing engine 212 may update the location of the centroid based on the re-estimated locations of the tips and/or ends of the one or more surgical tools. The estimation (and/or re-estimation) of the locations of the tips/ends of the one or more surgical tools is explained in detail in FIG. 2.

At step 912, poses of the one or more surgical tools in the video frame may be estimated. In accordance with an embodiment, the tool localizing engine 212 may be configured to estimate the poses of the one or more surgical tools, based on occlusion of the tips and/or ends of the one or more surgical tools. In accordance with an embodiment, the estimation of the poses of the one or more surgical tools may be based on the estimated locations of the ends of the one or more surgical tools, when the tips of the one or more surgical tools are occluded. Further, the estimation of the poses of the one or more surgical tools may be based on the estimated locations of the tips of the one or more surgical tools, when the centroid and/or the ends of the one or more surgical tools is/are occluded. Exemplary scenarios of poses of the one or more surgical tools are explained in detail in FIGS. 7A to 7D. Further, the estimation of the poses of the one or more surgical tools is explained in detail in FIG. 2. Control passes to end step 914.

In accordance with an embodiment of the disclosure, a system to localize surgical tools during anatomical surgery is disclosed. The system may comprise the image-processing server 104, communicatively coupled to the image-capturing device (not shown in FIG. 1), via the communication network 110. The image-capturing device may be configured to capture one or more video frames during the anatomical surgery. The image-processing server 104 may be configured to determine one or more physical characteristics of one or more surgical tools present in a video frame from the one or more video frames, based on one or more color and geometric constraints. The image-processing server 104 may be further configured to detect 2D masks of the one or more surgical tools present in the video frame, based on the determined one or more physical characteristics of the one or more surgical tools. In addition, the image-processing server 104 may be configured to estimate poses of the one or more surgical tools in the video frame, when the 2D masks of the one or more surgical tools are occluded at tips and/or ends of the one or more surgical tools.

Various embodiments of the disclosure may provide a non-transitory computer readable medium and/or storage medium, and/or a non-transitory machine readable medium and/or storage medium having stored thereon, a machine code and/or a computer program having at least one code section executable by a machine and/or a computer to localize surgical tools during anatomical surgery. The at least one code section in the image-processing server 104 may cause the machine and/or computer to perform the steps that comprise the determination of one or more physical characteristics of one or more surgical tools present in a video frame from one or more video frames, based on one or more color and geometric constraints. The one or more video frames may be captured by the image-capturing device, which may be communicatively coupled to the image-processing server 104, via the communication network 110. In accordance with an embodiment, 2D masks of the one or more surgical tools present in the video frame may be detected, based on the determined one or more physical characteristics of the one or more surgical tools. Further, poses of the one or more surgical tools in the video frame may be estimated, when the 2D masks of the one or more surgical tools are occluded at tips and/or ends of the one or more surgical tools.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted for carrying out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features enabling the implementation of the methods described herein, and which when loaded in a computer system is able to carry out these methods. Computer program, in the present context, means any expression, in any language, code or notation, of a set of instructions intended to cause a system with an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A system comprising:
one or more circuits configured to:
determine physical characteristics of a plurality of surgical tools based on color constraints of said plurality of surgical tools;
detect two-dimensional (2D) masks of said plurality of surgical tools in at least one video frame based on said physical characteristics of said plurality of surgical tools;
estimate poses of said plurality of surgical tools in said at least one video frame based on said 2D masks of said plurality of surgical tools; and
display masked at least one video frame based on said poses of said plurality of surgical tools.

2. The system of claim 1, wherein said one or more circuits are further configured to receive user input from a user terminal.

3. The system of claim 2, wherein said user input corresponds to at least one of a touch operation or a gesture by a user of said system.

4. The system of claim 1, wherein said one or more circuits are communicatively coupled with an image capturing device that is configured to capture said at least one video frame.

5. The system of claim 1, wherein said poses of said plurality of surgical tools are based on occlusion of said 2D masks of said plurality of surgical tools.

6. The system of claim 5, wherein said one or more circuits are further configured to generate a notification indicative of said occlusion of said plurality of surgical tools,
wherein said notification corresponds to at least one of an audio alert, a textual alert, a visual alert, or a haptic alert.

7. A method comprising:
determining physical characteristics of a plurality of surgical tools based on color constraints of said plurality of surgical tools;
detecting two-dimensional (2D) masks of said plurality of surgical tools in at least one video frame based on said physical characteristics of said plurality of surgical tools;
estimating poses of said plurality of surgical tools in said at least one video frame based on said 2D masks of said plurality of surgical tools; and
displaying masked at least one video frame based on said poses of said plurality of surgical tools.

8. The method of claim 7, further comprising receiving user input from a user terminal.

9. The method of claim 8, wherein said user input corresponds to at least one of a touch operation or a gesture by a user.

10. The method of claim 7, wherein said poses of said plurality of surgical tools are based on occlusion of said 2D masks of said plurality of surgical tools.

11. The method of claim 10, further comprising generating a notification indicative of said occlusion of said plurality of surgical tools, wherein said notification corresponds to at least one of an audio alert, a textual alert, a visual alert, or a haptic alert.

12. The method of claim 7, further comprising capturing said at least one video frame.

13. A non-transitory computer-readable medium having stored thereon computer-executable instructions that, when executed by a processor, cause the processor to execute operations, the operations comprising:
- determining physical characteristics of a plurality of surgical tools based on color constraints of said plurality of surgical tools;
- detecting two-dimensional (2D) masks of said plurality of surgical tools in at least one video frame based on said physical characteristics of said plurality of surgical tools;
- estimating poses of said plurality of surgical tools in said at least one video frame based on said 2D masks of said plurality of surgical tools; and
- displaying masked at least one video frame based on said poses of said plurality of surgical tools.

14. The non-transitory computer-readable medium of claim 13, further comprising receiving user input from a user terminal.

15. The non-transitory computer-readable medium of claim 14, wherein said user input corresponds to at least one of a touch operation or a gesture by a user.

16. The non-transitory computer-readable medium of claim 13, wherein said poses of said plurality of surgical tools are based on occlusion of said 2D masks of said plurality of surgical tools.

17. The non-transitory computer-readable medium of claim 16, further comprising generating a notification indicative of said occlusion of said plurality of surgical tools,
- wherein said notification corresponds to at least one of an audio alert, a textual alert, a visual alert, or a haptic alert.

* * * * *